(12) United States Patent
Emalfarb

(10) Patent No.: US 10,898,111 B2
(45) Date of Patent: Jan. 26, 2021

(54) BIOMEASUREMENT DEVICES WITH USER VERIFICATION AND METHODS OF USING THE SAME

(71) Applicant: MEDF LLC, Chicago, IL (US)

(72) Inventor: Michael Evan Emalfarb, Chicago, IL (US)

(73) Assignee: MEDF LLC, Chicago, IL (US)

( * ) Notice: Subject to any disclaimer, the term of this patent is extended or adjusted under 35 U.S.C. 154(b) by 84 days.

(21) Appl. No.: 15/866,447

(22) Filed: Jan. 9, 2018

(65) Prior Publication Data

US 2018/0125393 A1 May 10, 2018

Related U.S. Application Data

(63) Continuation of application No. 15/787,499, filed on Oct. 18, 2017, now Pat. No. 9,901,289, which is a continuation-in-part of application No. 15/490,869, filed on Apr. 18, 2017, now abandoned.

(60) Provisional application No. 62/324,781, filed on Apr. 19, 2016.

(51) Int. Cl.
| *A61B 5/1171* | (2016.01) |
| *G01G 19/44* | (2006.01) |
| *A61B 5/107* | (2006.01) |
| *G01G 19/50* | (2006.01) |
| *G01G 21/28* | (2006.01) |
| *G01G 23/37* | (2006.01) |
| *G01G 23/42* | (2006.01) |
| *G06K 9/00* | (2006.01) |

(52) U.S. Cl.
CPC .......... *A61B 5/1079* (2013.01); *A61B 5/1072* (2013.01); *A61B 5/1176* (2013.01); *G01G 19/44* (2013.01); *G01G 19/50* (2013.01); *G01G 21/283* (2013.01); *G01G 23/3728* (2013.01); *G01G 23/3735* (2013.01); *G01G 23/42* (2013.01); *G06K 9/00885* (2013.01); *A47G 2200/226* (2013.01)

(58) Field of Classification Search
CPC ...... G01G 19/44; G01G 19/50; G01G 21/283; G01G 23/3728; G01G 23/3835; G01G 23/42; A61B 5/1072; A61B 5/1079; A61B 5/1176

See application file for complete search history.

(56) References Cited

U.S. PATENT DOCUMENTS

| 8,901,442 B1 | 12/2014 | Dilone |
| 9,358,426 B2 | 6/2016 | Aragones |
| 9,498,137 B2 | 11/2016 | Kovacs |
| 9,901,289 B1 | 2/2018 | Emalfarb |

(Continued)

*Primary Examiner* — Natalie Huls
(74) *Attorney, Agent, or Firm* — Nixon Peabody LLP

(57) ABSTRACT

A method includes receiving, via an electronic scale device supporting a user thereon, an indication to begin a verified weight sequence. Responsive to the indication to begin, the method includes: (1) determining a body weight of the user supported by the electronic scale device, (2) receiving, via an electronic device, image data that is reproducible as a visual image of at least a portion of the user supported on the housing of the scale, and (3) generating a data file including: (a) weight data that is representative of the determined body weight of the user supported by the housing, (b) the image data, and (c) time data corresponding to a date and time that the body weight of the user was determined.

4 Claims, 18 Drawing Sheets

(56) References Cited

U.S. PATENT DOCUMENTS

| | | | |
|---|---|---|---|
| 10,515,309 B1* | 12/2019 | McNamara | G06Q 50/28 |
| 2002/0134589 A1 | 9/2002 | Montagnino | |
| 2010/0051353 A1 | 3/2010 | Swan | |
| 2014/0032234 A1 | 1/2014 | Anderson | |
| 2015/0045632 A1 | 2/2015 | Bagan | |
| 2015/0294641 A1 | 10/2015 | Jones | |
| 2015/0302721 A1 | 10/2015 | Schmidt | |
| 2016/0038037 A1* | 2/2016 | Kovacs | A61B 5/6887 |
| | | | 600/301 |
| 2016/0378924 A1* | 12/2016 | Bagan | G01G 19/50 |
| | | | 705/2 |
| 2017/0061224 A1* | 3/2017 | Moliner | G06F 3/041 |
| 2017/0143282 A1 | 5/2017 | Kovacs | |
| 2017/0188960 A1 | 7/2017 | Banet | |
| 2017/0206329 A1 | 7/2017 | Capocasale | |
| 2017/0220040 A1* | 8/2017 | London | A45C 5/145 |
| 2017/0300743 A1 | 10/2017 | Emalfarb | |
| 2018/0168517 A1* | 6/2018 | Wachi | A61B 5/4866 |
| 2018/0296136 A1* | 10/2018 | Foxlin | A61B 5/0531 |
| 2019/0362546 A1* | 11/2019 | Wayenberg | G06T 17/20 |

\* cited by examiner

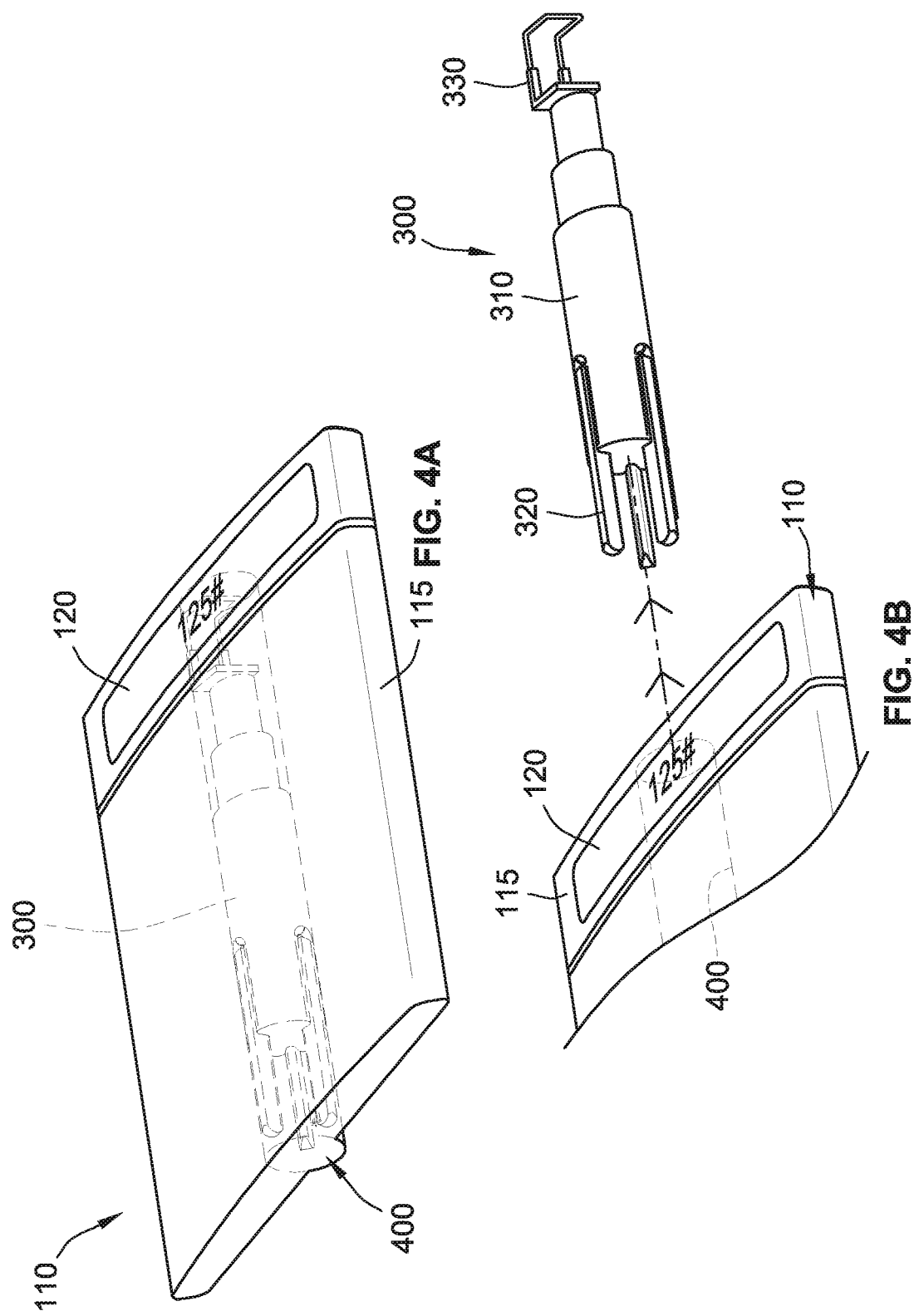

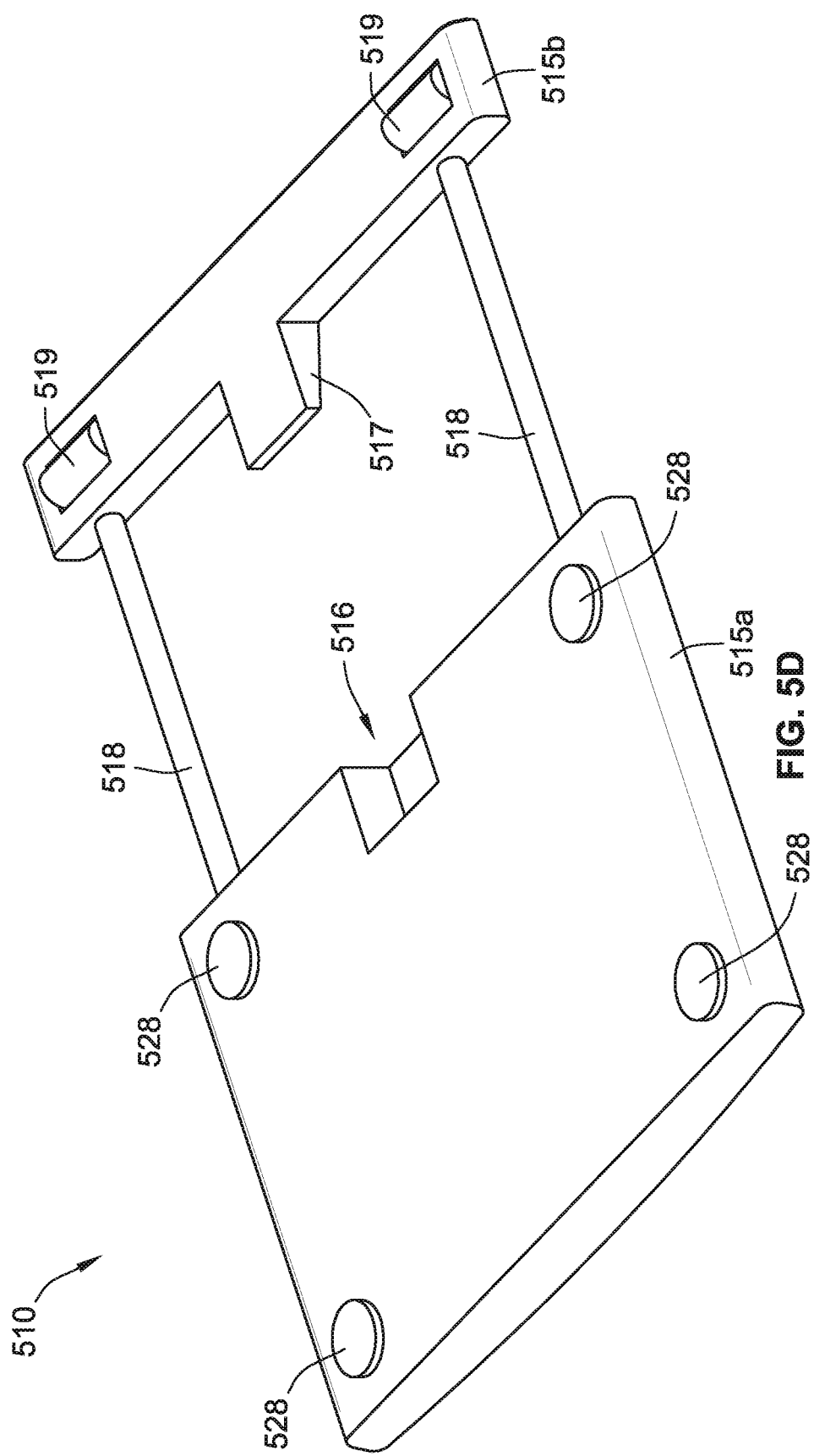

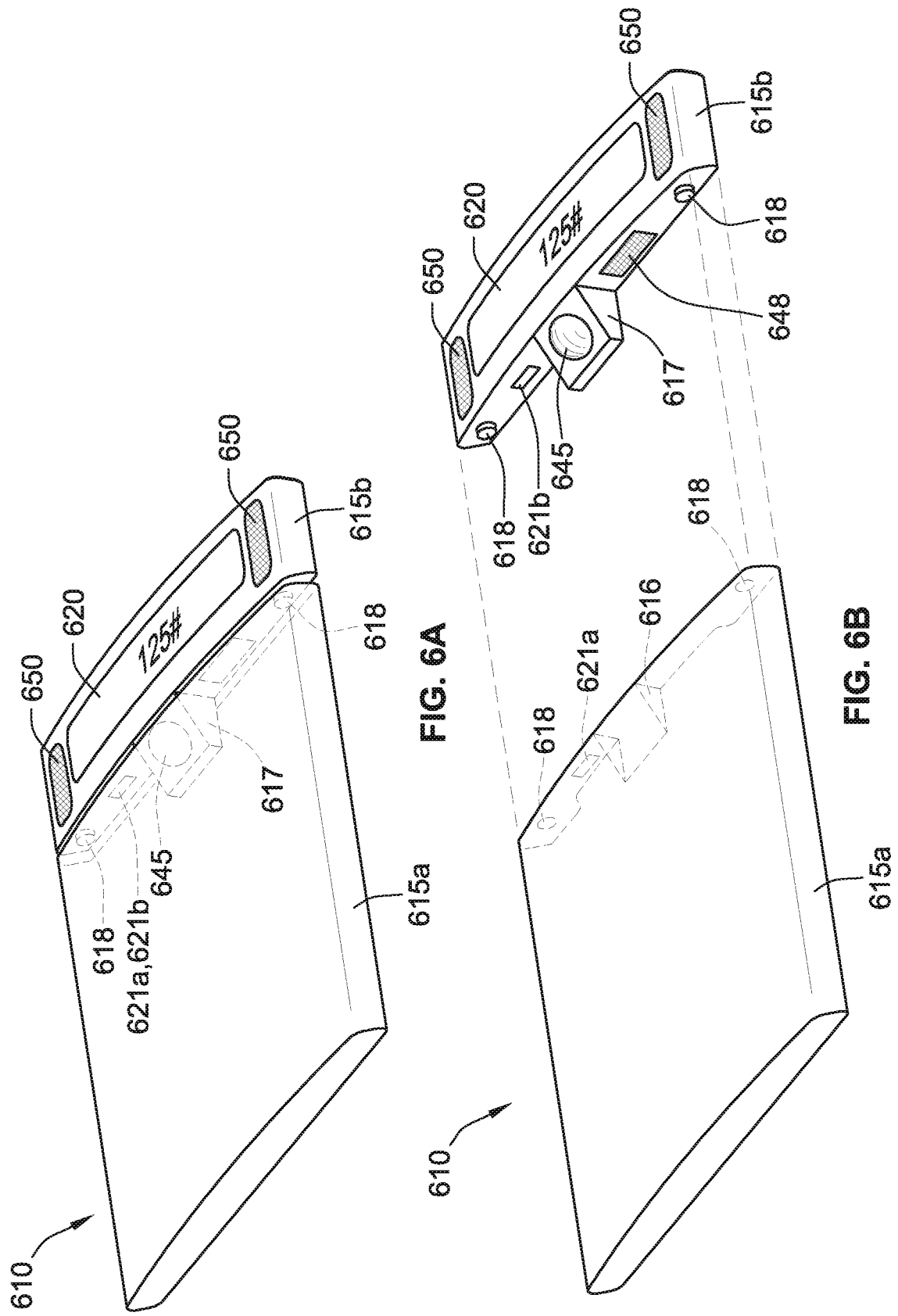

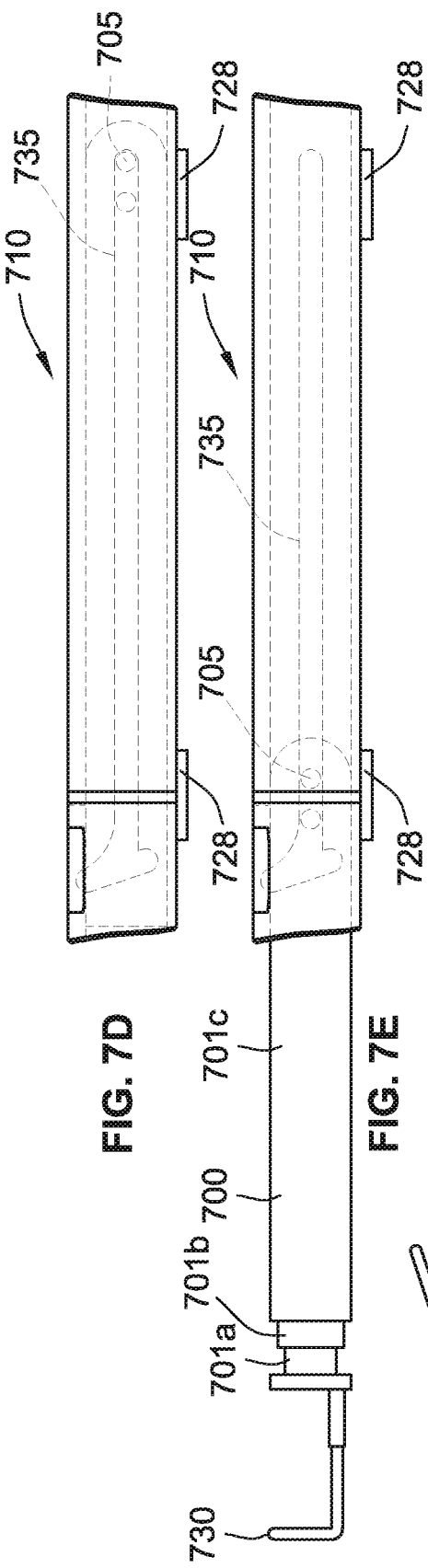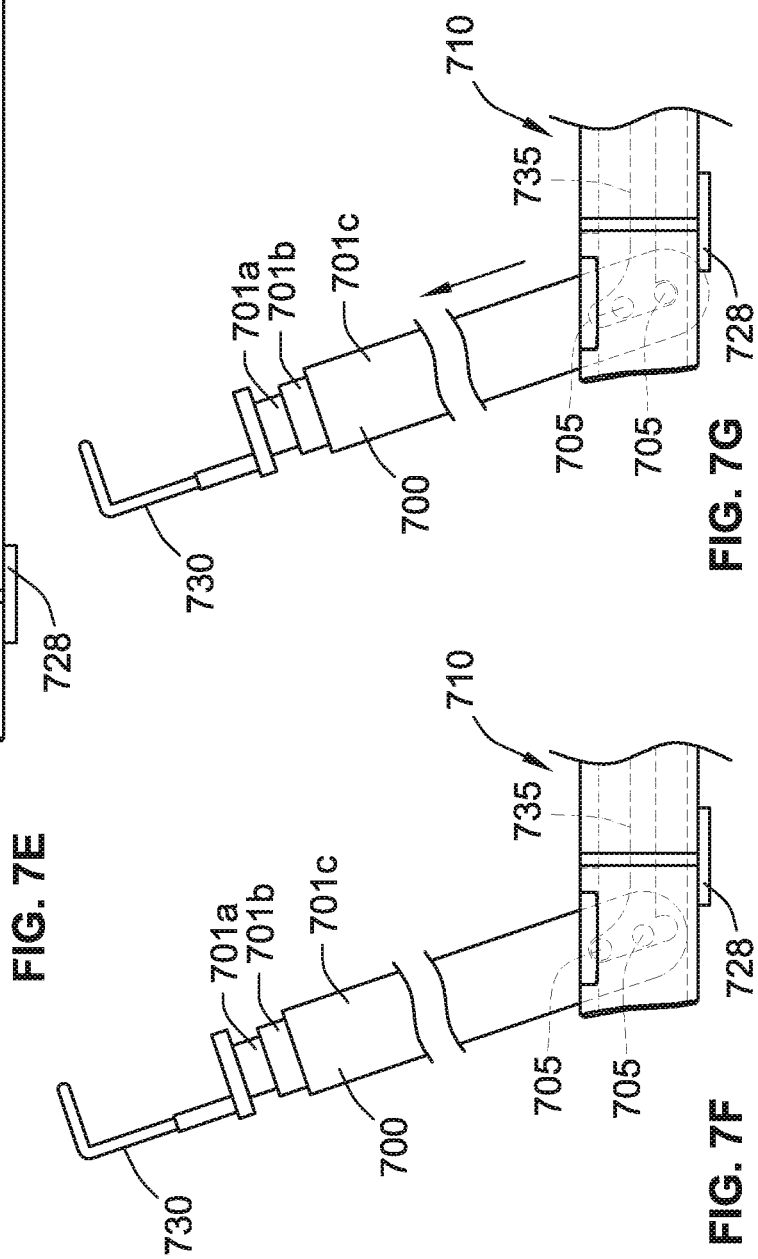

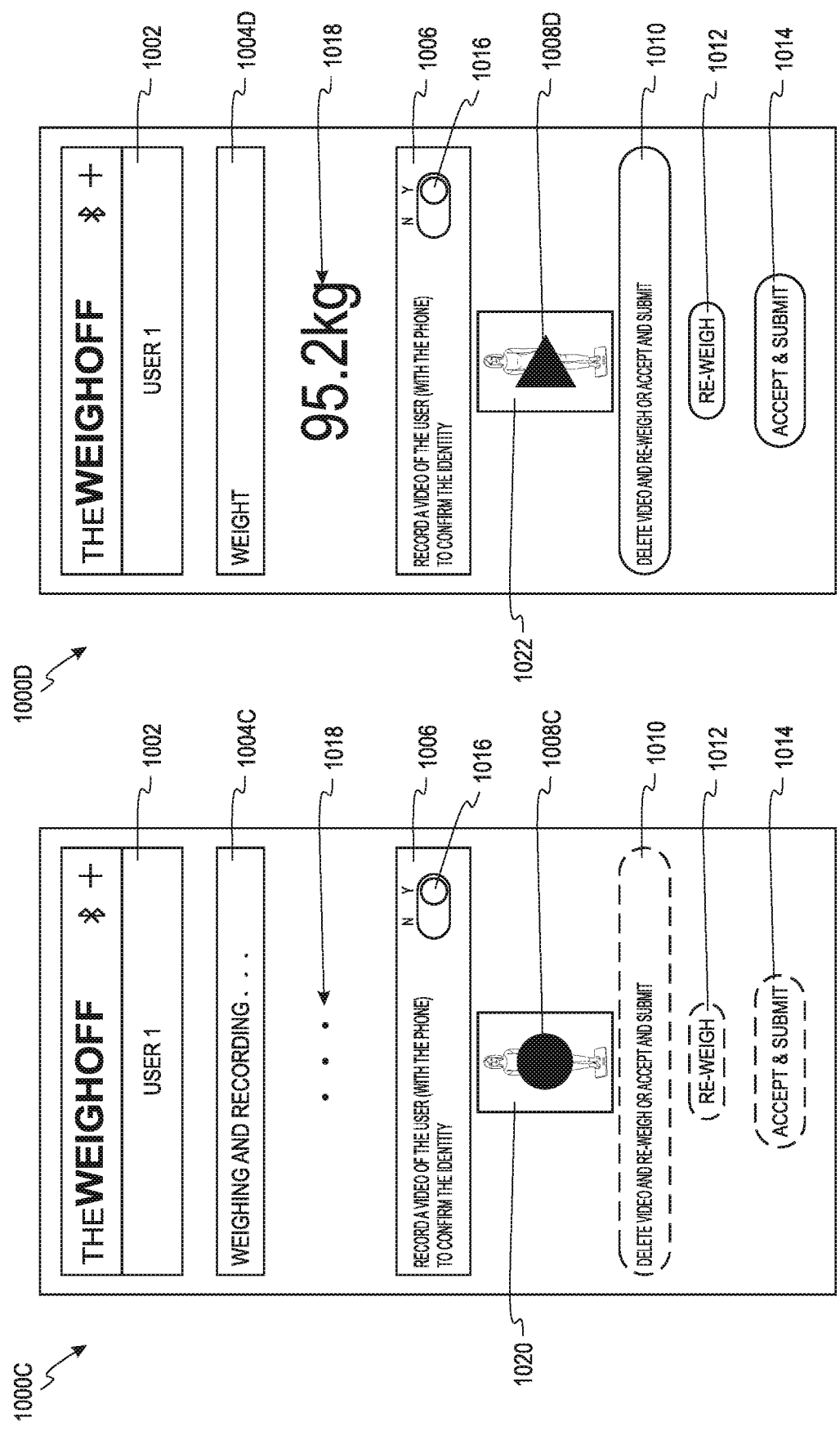

BIOMEASUREMENT DEVICES WITH USER VERIFICATION AND METHODS OF USING THE SAME

CROSS-REFERENCE TO RELATED APPLICATIONS

This application is a continuation of U.S. patent application Ser. No. 15/787,499, filed Oct. 18, 2017, now allowed, which is a continuation-in-part of U.S. patent application Ser. No. 15/490,869, filed Apr. 18, 2017, which claims the benefit of and priority to U.S. Provisional Application No. 62/324,781, filed Apr. 19, 2016, which is hereby incorporated by reference herein in its entirety.

TECHNICAL FIELD

This disclosure relates to biomeasurement devices with user verification systems and methods of using the same.

BACKGROUND

Weight loss competitions require users to conduct one or more weigh-ins to track performance. Preventing cheating is paramount to conducting a fair and enjoyable competition. Prior competitions completely ignore and/or leave room for error in the verification of a contestant's identify and/or accurate weight during a weigh-in. Thus, a need exists for a method and system to verify the identities of weight loss competition contests and to verify their weigh-ins. The present disclosure is directed to solving these problems and addressing other needs.

BRIEF SUMMARY

According to some implementations of the present disclosure, a scale includes a housing, an electronic display, a wireless communication module, one or more processors, and a memory device. The housing is configured to support a user thereon. The electronic display is coupled to the housing for displaying a body weight of the user. The wireless communication module is configured to wirelessly communicate with an electronic device. The memory device stores instructions that, when executed by at least one of the one or more processors, cause the scale to: (1) determine the body weight of the user supported by the housing, and (2) wirelessly transmit instructions to the electronic device. The instructions direct the electronic device to generate image data that is reproducible as a visual image of the user supported on the housing of the scale at about the same time that the scale determines the body weight of the user.

According to some implementations of the present disclosure, a scale includes a housing, an electronic display, a wireless communication module, one or more processors, and a memory device. The housing is configured to support a user thereon. The electronic display is coupled to the housing for displaying a body weight of the user. The wireless communication module is configured to wirelessly communicate with an electronic device. The memory device stores instructions that, when executed by at least one of the one or more processors, cause the scale to: (1) determine the body weight of the user supported by the housing, (2) wirelessly access the electronic device to cause the electronic device to generate image data that is reproducible as a visual image of the user supported on the housing of the scale, and (3) wirelessly receive the image data from the electronic device.

According to some implementations of the present disclosure, a digital bathroom scale for use in a weight loss competition includes a housing, an electronic display, a wireless communication module, one or more processors, and a memory device. The housing is configured to support a user thereon. The electronic display is coupled to the housing for displaying a body weight of the user. The wireless communication module is configured to wirelessly communicate with an electronic device. The memory device stores instructions that, when executed by at least one of the one or more processors, cause the scale to: (1) determine the body weight of the user supported by the housing and (2) wirelessly transmit weight data representative of the body weight of the user supported by the housing, via the wireless communication module, to the electronic device for inclusion in a data file. Responsive to the wireless transmission of the weight data, the electronic device: (A) generates image data that is reproducible as a visual image of the user supported on the housing of the scale, and (B) wirelessly transmits, via a wireless communication module of the electronic device, the data file to a server for verification of the body weight of the user. The data file includes the weight data, the image data, and time data corresponding to a date and time that the body weight of the user was determined.

According to some implementations of the present disclosure, a weight verification system includes a scale having a housing, an electronic display, one or more processors, a wireless communication module, and a memory device storing instructions that, when executed by at least one of the one or more processors, cause the system to: (1) determine a body weight of a user supported by the housing of the scale and (2) generate image data that is reproducible as a head-to-toe visual image of the user supported on the housing of the scale at about the same time that the scale determines the body weight of the user.

According to some implementations of the present disclosure, a method includes receiving, via an electronic scale device supporting a user thereon, an indication to begin a verified weight sequence. Responsive to the indication to begin, the method includes: (1) determining a body weight of the user supported by the electronic scale device, (2) receiving, via an electronic device, image data that is reproducible as a visual image of at least a portion of the user supported on the housing of the scale, and (3) generating a data file including (a) weight data that is representative of the determined body weight of the user supported by the housing, (b) the image data, and (c) time data corresponding to a date and time that the body weight of the user was determined.

According to some implementations of the present disclosure, a method of conducting a verified weigh-in includes wirelessly registering an electronic device with the scale. The electronic device has a front-facing camera and a rear-facing camera. A user is detected on a scale. A body weight of the user on the scale is determined. The scale receives a unique indicium. The unique indicium is displayed, on a display device of the scale. The determined body weight of the user is displayed on the display device of the scale. The front-facing camera is caused to take a picture of at least a portion of a face of the user on the scale simultaneously with the rear-facing camera taking a picture of: (a) at least a portion of feet of the user on the scale, and (b) at least a portion of the display of the scale displaying the unique indicium and the determined body weight of the user.

According to some implementations of the present disclosure, a method of conducting a verified weigh-in includes wirelessly registering an electronic device with the scale.

The electronic device has a front-facing camera and a rear-facing camera. A user is detected on a scale. A body weight of the user on the scale is determined. A unique indicium received by the scale from the electronic device is displayed on a display device of the scale. The front-facing camera is caused to take a picture of at least a portion of a face of the user on the scale simultaneously with the rear-facing camera taking a picture of: (a) at least a portion of feet of the user on the scale, and (b) at least a portion of the display of the scale displaying the unique indicium. Weight data representative of the determined body weight of the user on the scale is wireless transmitted to the electronic device for inclusion in a data file.

According to some implementations of the present disclosure, a method of conducting a verified weigh-in includes detecting a user on a scale. A body weight of the user on the scale is determined. The determined body weight of the user on the scale is displayed on a display device of the scale. A front-facing camera of an electronic device is caused to take a picture of at least a portion of a face of the user on the scale simultaneously with a rear-facing camera of the electronic device taking a picture of: (a) at least a portion of feet of the user on the scale and (b) at least a portion of the display of the scale displaying the determined body weight of the user.

According to some implementations of the present disclosure, a scale includes a housing, an electronic display, and an extendible member. The housing is configured to support a user thereon. The electronic display is coupled to the housing for displaying a body weight of the user. The extendible member is coupled to the housing and is movable between a collapsed-storage position and an extended-generally-upright position.

According to some implementations of the present disclosure, a scale for use with an electronic device to conduct verified weigh-ins includes a housing, an electronic display, a wireless communication module, one or more processors, a memory device, an extendible member, a coupling mechanism, and a pivotable-pin assembly. The housing is configured to support a user thereon. The electronic display is coupled to the housing for displaying a body weight of the user. The wireless communication module is configured to wirelessly communicate with the electronic device. The memory device stores instructions that, when executed by at least one of the one or more processors, cause the scale to determine the body weight of the user supported by the housing. The extendible member is coupled to the housing and is movable between a collapsed-storage position and an extended-generally-upright position. A central axis of the extendible member is generally horizontal in the collapsed-storage position and is at an angle between about 30 degrees and about 90 degrees relative to horizontal in the extended-generally-upright position. The coupling mechanism extends from a first end of the extendible member. The coupling mechanism is configured to releasably hold the electronic device in a generally fixed position relative to the housing. The pivotable-pin assembly is coupled to a second opposing end of the extendible member. The pivotable-pin assembly is slidable from a first end of a track to a second end of the track such that the extendible member can (i) slide relative to the housing and (ii) pivot relative to the housing. The extendible member is releasably maintained in the extended-generally-upright position by the pivotable-pin assembly engaging the second end of the track.

According to some implementations of the present disclosure, a scale includes a main housing and a movable housing. The main housing is configured to support a user thereon. The movable housing is coupled to the main housing via a pair of rods. The movable housing is movable between a first position adjacent to the main housing and a second position spaced from the main housing. The movable housing includes an electronic display for displaying a body weight of the user. The movable housing further includes a camera for generating image data that is reproducible as a visual image or a visual video clip of at least a portion of the user supported on the main housing of the scale. A lens of the camera is obscured by the main housing when the movable housing is in the first position and the lens of the camera is not obscured by the main housing when the movable housing is in the second position.

According to some implementations of the present disclosure, a scale system includes a main housing, a rotating housing, and a camera. The main housing includes an electronic display for displaying a body weight of the user. The rotating housing is coupled to the main housing via a drive system. The rotating housing is rotatable about the main housing. The camera is for generating image data that is reproducible as a visual image or a visual video clip of at least a portion of the user supported on the main housing of the scale.

According to some implementations of the present disclosure, a scale system includes a scale housing, an electronic display, and an extendible member. The scale housing is configured to support a user thereon. The electronic display is coupled to the scale housing for displaying a body weight of the user. The extendible member has a collapsed configuration and an extended configuration. The extendible member includes a coupling mechanism extending from a first end of the extendible member. The coupling mechanism is configured to releasably hold an electronic device in a generally fixed position relative to the scale housing. The extendible member includes a base-plate extending from a second opposing end of the extendible member. The base-plate is configured to be positioned under the scale housing when the user is supported on the scale housing.

According to some implementations of the present disclosure, a method includes receiving at a first time, via an electronic scale device supporting a user thereon, a first indication to begin a first verified weight sequence. Responsive to the first indication to begin the first verified weight sequence, the method includes: (1) determining a first body weight of the user supported by the electronic scale device, (2) receiving, via an electronic device, first image data that is reproducible as a first visual image of at least a portion of the user supported on the housing of the scale, and (3) analyzing the first image data using recognition software to produce a first user appearance profile. An expected user appearance profile is created based on at least the first user appearance profile. The method further includes receiving at a second time, via the electronic scale device supporting the user thereon, a second indication to begin a second verified weight sequence. Responsive to the second indication to begin the second verified weight sequence, the method includes: (1) determining a second body weight of the user supported by the electronic scale device, (2) receiving, via an electronic device, second image data that is reproducible as a second visual image of at least a portion of the user supported on the housing of the scale, (3) analyzing the second image data using recognition software to produce a second user appearance profile, and (4) comparing the second user appearance profile to the expected user appearance profile.

According to some implementations of the present disclosure, a method of conducting a verified weigh-in includes generating, via an electronic device, video data that is reproducible as a visual video clip of at least a portion of a user supported on a scale. The visual video clip is displayed, in real-time, on a display device of the electronic device. First time data is overlaid, in real-time, on the displayed visual video clip. The first time data corresponds to a range of time that the video data was generated by the electronic device. Scale data is received, from the scale supporting the user. The scale data includes a determined weight of the user and second time data. The second time data corresponds to a time that the weight of the user was determined by the scale. The determined weight of the user and the second time data are overlaid on the displayed visual video clip.

According to some implementations of the present disclosure, a method of conducting a verified weigh-in includes generating, via an electronic device, video data that is reproducible as a visual video clip of at least a portion of a user supported on a scale. The generated video data is modified to embed therein first time data. The first time data corresponds to a range of time that the video data was generated by the electronic device. Scale data is received from the scale supporting the user. The scale data includes a determined weight of the user and second time data. The second time data corresponds to a time that the weight of the user was determined by the scale. The generated video data is modified to embed therein the determined weight of the user and the second time data.

According to some implementations of the present disclosure, a method of conducting a verified biomeasurement of a user includes generating, via an electronic device, video data that is reproducible as a visual video clip of at least a portion of a user adjacent to a biomeasurement device. The generated video data is modified to embed therein first time data. The first time data corresponds to a range of time that the video data was generated by the electronic device. Second time data and a determined biomeasurement associated with the user are received from the biomeasurement device adjacent to the user. The second time data corresponds to a time that the biomeasurement associated with the user was determined by the biomeasurement device. The generated video data is modified to embed therein the determined biomeasurement associated with the user and the second time data.

According to some implementations of the present disclosure, a method includes receiving, from a biomeasurement device associated with a user, an indication to begin a verified measurement sequence. Responsive to the indication to begin, video data that is reproducible as a visual video clip of at least a portion of a user and at least a portion of the biomeasurement device is received from a camera of an electronic device. A biomeasurement of the user associated with the biomeasurement device is received from the biomeasurement device. A data file is generated that includes (a) the determined biomeasurement, (b) at least a portion of the video data, and (c) first time data corresponding to a time that the biomeasurement of the user was determined by the biomeasurement device.

The foregoing and additional aspects and implementations of the present disclosure will be apparent to those of ordinary skill in the art in view of the detailed description of various embodiments and/or implementations, which is made with reference to the drawings, a brief description of which is provided next.

BRIEF DESCRIPTION OF THE DRAWINGS

The foregoing and other advantages of the present disclosure will become apparent upon reading the following detailed description and upon reference to the drawings.

FIG. 4A is a perspective view of a scale with a free-standing extendible member stored in a housing of the scale according to some implementations of the present disclosure;

FIG. 4B is a perspective view of the scale of FIG. 4A illustrating the free-standing extendible member being removed from the scale;

FIG. 5D is a bottom perspective view of the scale of FIG. 5A with the movable housing in the extended position;

FIG. 6A is a top perspective view of a scale with a detachable housing attached to a main housing according to some implementations of the present disclosure;

FIG. 6B is a top perspective view of the scale of FIG. 6A with the detachable housing detached from and spaced away from the main housing;

FIG. 7D is a side view of the scale of FIG. 7A with the extendible member in the collapsed-storage position;

FIG. 7E is a side view of the scale of FIG. 7A with the extendible member extending from the housing of the scale in the collapsed and generally horizontal position;

FIG. 7F is a partial side view of the scale of FIG. 7A with the extendible member in a collapsed-generally-upright position and a pivotable-pin assembly of the extendible member in a first position;

FIG. 7G is a partial side view of the scale of FIG. 7A with the extendible member in the collapsed-generally-upright position and the pivotable-pin assembly of the extendible member in a second position;

FIG. 10C is a front view of a user interface at a third time during a verified weight sequence;

FIG. 10D is a front view of a user interface at a fourth time during a verified weight sequence;

Figure 1:
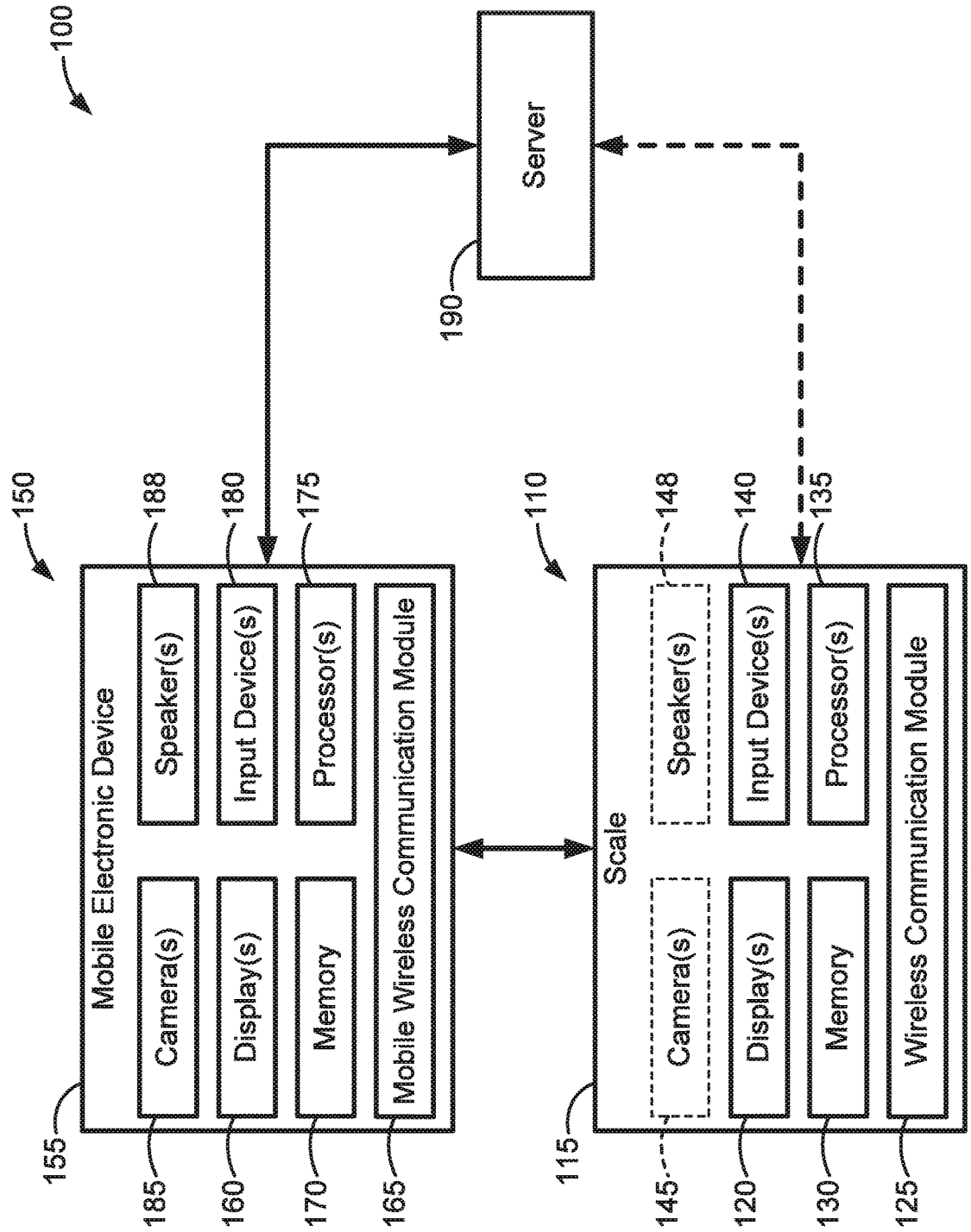
FIG. 1 is a schematic view of a weight verification system according to some implementations of the present disclosure.

While the present disclosure is susceptible to various modifications and alternative forms, specific implementations have been shown by way of example in the drawings and will be described in detail herein. It should be understood, however, that the present disclosure is not intended to be limited to the particular forms disclosed. Rather, the present disclosure is to cover all modifications, equivalents, and alternatives falling within the spirit and scope of the present disclosure as defined by the appended claims.

DETAILED DESCRIPTION

Referring generally to FIG. 1, a weight verification system 100 includes a scale 110 (e.g., a biomeasurement device), a mobile electronic device 150, and a server 190. The scale 110 can be a smart scale, a WiFi scale, a spring scale, a digital scale, a bathroom scale, or any combination thereof. The server 190 can be local (e.g., in the same house or building as the scale 110 and the mobile electronic device 150) or remote (e.g., in a different building, in a different state, in a different country). The server 190 is communicatively coupled (e.g., over the interne, over one or more wired and/or wireless networks, etc.) to the scale 110 and/or the mobile electronic device 150 to receive data files for evaluation. The data files can include a variety of information used to: (1) verify an identity of a participant in the weight loss competition, (2) verify a weight or weigh-in of the participant, (3) evaluate weigh-ins for cheating, etc. In some implementations, the data files include weight data (e.g., data that is representative of a body weight of a user), image data (e.g., image data that is reproducible as a visual image of a user), and time data (e.g., data corresponding to a date and time that a body weight of a user was determined and/or data corresponding to a date and time that one or more pictures of a user were captured). The verification functions of the server 190 are performed using one or more software programs running on (e.g., executing on) the server 190 that automatically analyze the data files and make determinations thereof (e.g., determinations of identity, cheating, accurate weight ins, etc.) for use in policing and/or conducting weight loss competitions.

Alternatively, instead of including a server 190, the verification functions can be conducted on the scale 110 and/or on the mobile electronic device 150. In some such alternative implementations, a verification result (e.g., a data file including information related to a determination as to whether the user's identify was verified, a determination as to whether the user's weigh-in was verified, a determination as to whether the user was cheating, etc., or any combination thereof) can be transmitted from the scale 110 and/or from the mobile electronic device 150 to the server 190 and/or a different server (not shown) for review and/or storage.

The scale 110 of the weight verification system 100 includes a housing 115 that can have any shape or size and be made of any material, such as, for example, plastic, metal (e.g., aluminum, steel, titanium), rubber, or any combination thereof. Exemplary housings are shown in various other implementations herein. The housing 115 is coupled to an electronic display 120 that is viewable and able to display a variety of information. For example, the electronic display 120 can display a determined weight of a user of the system 100, a time and date of a weight determination (i.e., the time that the scale 110 determined the weight of the user), preprogramed and/or received messages (e.g., "Keep up the good work"; "Stop eating cupcakes"; "Get to work"; etc.), instructions for conducting a weigh-in session, instructions for using an application running on the mobile electronic device 150, instructions for operating the scale 110, or any other type of information.

The housing 115 of the scale 110 also includes therein a wireless communication module 125 for establishing and/or communicating wirelessly with the mobile electronic device 150 and/or the server 190 (e.g., directly and/or indirectly via the mobile electronic device 150). The wireless communication module 125 can communicate using any type of wireless technology, such as, for example, Bluetooth, Bluetooth Low Energy (BLE), WiFi, Near Field Communication (NFC), ZigBee, Mesh Networking, Worldwide Interoperability for Microwave Access (WiMax), Radio Frequency (RF), Infrared (IR), etc., or any combination thereof. For example, in some implementations, the wireless communication module 125 establishes communication between the scale 110 and the mobile electronic device 150 via BLE and establishes communication between the scale 110 and the server 190 via WiFi.

The housing 115 of the scale 110 also includes therein a memory 130 and one or more processors 135. The memory 130 stores instructions that are executable by the one or more processors 135 to cause the scale 110 to perform a multitude of functions. For example, execution of the instructions stored on the memory 130 cause the scale 110 to determine a body weight of a user supported on (e.g., standing on) the housing 115 of the scale 110. For another example, execution of the instructions stored on the memory 130 cause the scale 110 to measure body fat of the user, a body mass index (BMI) of the user, a lean mass of the user, a muscle mass of the user, a water ratio of the user, or any combination thereof. For yet another example, execution of the instructions stored on the memory 130 cause the scale 110 to wirelessly transmit weight data representative of the determined body weight of the user supported by the housing 115, via the wireless communication module 125, to the mobile electronic device 150 and/or the server 190.

For yet another example, execution of the instructions stored on the memory 130 cause the scale 110 to wirelessly transmit instructions to the mobile electronic device 150. In some such implementations, the transmitted instructions direct the mobile electronic device 150 to generate image data that is reproducible as a visual image of the user supported on the housing 115 of the scale 110 at about the same time that the scale 110 determines the body weight of the user.

In some implementations, the scale 110 includes one or more input devices 140. The input device 140 can be a touch screen, a softkey on a touch screen, a physical button (e.g., a toe-push-button), a joystick, a toe-print scanner (e.g., scanner to scan a toe-print of the user for use in identifying the user), or any other type of input device that permits a user to select options displayed on the display device 120 and/or to initiate a verified weigh-in sequence. In some such implementations including a toe-push button as an input device 140 of the scale 110, the toe-push-button 140 protrudes from a surface of the housing 115 of the scale 110 such that the toe-push-button 140 is readily accessible by the user to be manually activated. Activation of the toe-push-button 140 by the user can (1) initiate a verified weigh-in sequence, (2) cause the one or more processors 135 to cause the scale 110 to determine the body weight of the user supported by the housing 115, (3) cause a camera 145 of the scale 110 to take one or more pictures, (4) cause a camera 185 of the mobile electronic device 150 to take one or more pictures, (5) record time stamp information (e.g., a date and time that the verified weigh-in sequence occurred), (6) generate a data file, (7) transmit a data file to the server 190, or any combination thereof.

The toe-push-button 140 is sized and positioned relative to the housing 115 of the scale 110 such that the toe-push-button 140 is generally accessible by a toe of the user when standing on the housing 115 of the scale 110. In some implementations, the toe-push-button 140 has an exposed surface area between about 0.05 square inches and about 4.0 square inches. In some other implementations, the toe-push-button 140 has an exposed surface area between about 0.25 square inches and about 1.0 square inch. In some other implementations, the toe-push-button 140 has an exposed surface area of about 0.4 square inches.

In some implementations, the scale 110 includes one or more cameras 145. The one or more cameras 145 can include standard cameras used to take color still images and/or color video, infrared cameras, thermal cameras, ultraviolet cameras, or a combination thereof. The one or more cameras 145 can be used to identify a user of the scale 110 via facial recognition software operating on the scale 110 or on any other device of the weight verification system 100. Additionally or alternatively the one or more cameras 145 can be used to generate image data for inclusion in a data file for use in verification of the user's identify and/or weigh-in as described herein. In some implementations, the image data is reproducible as a head-to-toe visual image of the user that includes at least a portion of the user's head and at least a portion of the user's feet (and everything in-between). In some alternative implementations, the image data is reproducible as a partial head-to-toe visual image of the user that does not include the user's head. In some other alternative implementations, the image data is reproducible as a visual image one or more portions of the user's body, such as, for example, the user's head, face, feet, mid-section/torso, legs, etc., or any combination thereof.

In some implementations, the scale 110 includes one or more speakers 148 coupled to the housing 115. The one or more speakers 148 can play a variety of audio clips, such as, for example, music, audio instructions, audio taunts (e.g., in response to the wireless communication module 125 of the scale 110 receiving a taunt signal), prerecorded audio messages, or any combination thereof.

The mobile electronic device 150 can be, for example, a cellphone (e.g., a smart phone, an iPhone® smart phone, an Android® smart phone), a tablet computer (e.g., an iPad®), a camera (e.g., a wireless or smart camera), or the like. The mobile electronic device 150 includes a housing 155 that can have any shape or size and be made of any material, such as, for example, plastic, metal (e.g., aluminum, steel, titanium), rubber, or any combination thereof.

The housing 155 of the mobile electronic device 150 is coupled to a mobile electronic display 160 that is viewable and able to display a variety of information. For example, the mobile electronic display 160 can display an application or app running on the mobile electronic device 150, one or more pictures of the user of the system 100 (e.g., standing on the housing 115 of the scale 110), a time and date that the one or more pictures were taken by one or more cameras 185 of the mobile electronic device 150 and/or by the one or more cameras 145 of the scale 110), a time and date of a weight determination (i.e., the time that the scale 110 determined the weight of the user), preprogramed and/or received messages (e.g., the following messages can be displayed: "Keep up the good work"; "Stop eating cupcakes"; "Get to work"; etc.), instructions for conducting a weigh-in session, instructions for using the application running on the mobile electronic device 150, instructions for operating the scale 110, or any other type of information.

The housing 155 of the mobile electronic device 150 also includes therein a mobile wireless communication module 165 for establishing and/or communicating wirelessly with the scale 110 and/or the server 190 (e.g., directly and/or indirectly via the scale 110). The wireless communication module 165 can communicate using any type of wireless technology, such as, for example, Bluetooth, Bluetooth Low Energy (BLE), WiFi, Near Field Communication (NFC), ZigBee, Mesh Networking, Worldwide Interoperability for Microwave Access (WiMax), Radio Frequency (RF), Infrared (IR), etc., or any combination thereof. For example, in some implementations, the wireless communication module 165 establishes communication between the mobile electronic device 150 and the scale 110 via BLE and establishes communication between the mobile electronic device 150 and the server 190 via WiFi. For another example, in some implementations, the wireless communication module 165 establishes communication between the mobile electronic device 150 and the scale 110 via WiFi and establishes communication between the mobile electronic device 150 and the server 190 via WiFi.

The housing 155 of the mobile electronic device 150 also includes therein a memory 170 and one or more processors 175. The memory 170 stores instructions that are executable by the one or more processors 175 to cause the mobile electronic device 150 to perform a multitude of functions. For example, execution of the instructions stored on the memory 170 cause the mobile electronic device 150 to: (1) wirelessly transmit, via the mobile wireless communication module 165, a data file to the server 190, (2) wirelessly transmit, via the mobile wireless communication module 165, image data to the scale 110 and/or the server 190, (3) verify an identify of a user of the scale 110, (4) verify a weigh-in conducted using the scale 110, etc., or any combination thereof.

The mobile electronic device 150 further includes one or more input devices 180. The input devices 180 can be a touch screen, a softkey on a touch screen, a physical button (e.g., a home button, a volume button, a power button, a shutter button, etc.), a joystick, or any other type of input device that permits a user to: (1) initiate a verified weigh-in sequence, (2) select options displayed on the display device 160, (3) operate the mobile electronic device, (4) transmit a data file to the server 190 for verification of a weigh-in, etc., or any combination thereof.

The mobile electronic device 150 includes one or more cameras 185. The one or more cameras 185 can include standard cameras used to take color still images and/or color video, infrared cameras, thermal cameras, ultraviolet cameras, or a combination thereof. The one or more cameras 185 can be used to identify a user of the mobile electronic device 150 and/or of the scale 110 via facial recognition software operating on the mobile electronic device 150. Additionally or alternatively the one or more cameras 185 can be used to generate image data (e.g., one or more pictures) for inclusion in a data file for use in verification of the user's identify and/or weigh-in as described herein. In some implementations, the image data is reproducible as a head-to-toe visual image of the user that includes at least a portion of the user's head and at least a portion of the user's feet (and everything in-between). In some alternative implementations, the image data is reproducible as a partial head-to-toe visual image of the user that does not include the user's head. In some other alternative implementations, the image data is reproducible as a visual image one or more portions of the user's body, such as, for example, the user's head, face, feet, mid-section/torso, legs, etc., or any combination thereof.

In some implementations, the mobile electronic device 150 includes a front-facing camera and a rear-facing camera. In some of such implementations, the front-facing camera is caused to (e.g., after initiation of a verified weigh-in sequence) take a picture of at least a portion of a face of the user on the scale 110 and the rear-facing camera is caused to take a picture of (a) at least a portion of feet of the user on the scale 110, and (b) at least a portion of the display 120 of the scale 110 displaying information, such as, for example, a unique indicium, a symbol, an alphanumeric code, a word, a number, a determined body weight of the user, a time, a date, a message, instructions, etc., or any combination thereof. In some such implementations, the front-facing camera and the rear-facing camera take the pictures simultaneously (e.g., at exactly the same time or about the same time).

The mobile electronic device 150 includes one or more speakers 188 coupled to the housing 155. The one or more speakers 188 can play a variety of audio clips, such as, for example, music, audio instructions (e.g., instructions on how to conduct a verified weigh-in, instructions on how to use the system 100, etc.), audio taunts (e.g., in response to the mobile wireless communication module 165 of the mobile electronic device 150 receiving a taunt signal), prerecorded audio messages, or any combination thereof.

A method of conducting a verified weigh-in using the weight verification system 100 is now described. The verified weigh-in begins when weight verification system 100 receives an indication to begin a verified weight sequence. The indication can caused by (1) a user stepping onto the scale 110, (2) a user activating the toe-push-button 140, (3) a user activating one of the input devices 180 of the mobile electronic device 150, or any combination thereof. After the initiation of the verified weigh-in, the scale 110 determines a body weight of the user standing on the housing 115. At about the same time or at exactly the same time that the scale 110 determines a body weight, image data is generated and/or received that is reproducible as one or more visual images and/or one or more visual videos of at least a portion of the user standing on the housing 115 of the scale 110. The image data can be generated by the camera 145 of the scale 110 and/or by the camera 185 of the mobile electronic device 150. In some alternative implementations, the image data is generated and/or received within five second of the time that the body weight is determined by the scale 110. In yet some other alternative implementations, the image data is generated and/or received within four, three, two, one, or less seconds of the time that the body weight is determined by the scale 110. By generating the image data (e.g., taking a picture and/or video) at the exact same time or about the same time that the body weight is determined, the ability for a contestant to cheat is reduced and/or eliminated.

In some implementations, the body weight and/or the image data is determined multiple times during a single weigh-in. For example, the user first stands on the scale 110 facing a first direction and then the user stands on the scale 110 facing another direction. As such, the weight verification system 100 is able to capture multiple angles (e.g., a front facing angle and a rear facing angle) of the user/contestant during the weigh-in.

In some implementations, a data file is generated that includes (a) weight data that is representative of the determined body weight of the user standing on the housing 115 of the scale 110, (b) the image data, and (c) time data corresponding to a date and time that the body weight of the user was determined and/or corresponding to a date and time that the image data was generated and/or received/transmitted. The data file can be generated by the scale 110, the mobile electronic device 150, the server 190, or a combination thereof.

In some implementations, the generated data file is transmitted. For example, if the mobile electronic device 150 generates the data file, the mobile electronic device 150 transmits the data file to the server 190 and/or the scale 110 for further processing and/or evaluation (e.g., conducting a verification function). Alternatively, if the scale 110 generates the data file, the scale 110 transmits the data file to the server 190 and/or to the mobile electronic device 150 for further processing and/or evaluation (e.g., conducting a verification function). In some implementations, prior to the data file being transmitted, the user is prompted to review the contents of the data file, or a portion thereof (e.g., the picture(s) of the user), and accept or reject the verified weigh-in. If the verified weigh-in is accepted by the user, then the data is automatically transmitted; however, if the verified weigh-in is rejected by the user, then the data is not transmitted and the user is prompted to conduct a second verified weigh-in sequence. The prompting can be displayed on the display devices and/or played on the speakers of the scale 110, of the mobile electronic device 150, or a combination thereof.

The data file is analyzed to conduct verification functions. For example, the image data in the data file can be analyzed using facial recognition software to verify the identity of the user. For another example, the image data in the data file can be analyzed using weight verification software to verify the determined body weight of the user. In some such implementations, the weight verification software compares one or more aspects of the image data (e.g., picture of the user) and/or the determined body weight with one or more corresponding aspects of other (e.g., older) data files associated with the user to determine if the newly/recently determined body weight is accurate or indicates potential cheating or unsafe weight loss practices. In some implementations, the weight verification software compares an outline of the user's body as depicted in the image data with one or more previous outlines of the user's body (as depicted in previously taken pictures of the user using the weight verification system 100) to verify the weigh-in (e.g., determine cheating, unsafe practices, etc.).

Figure 2:
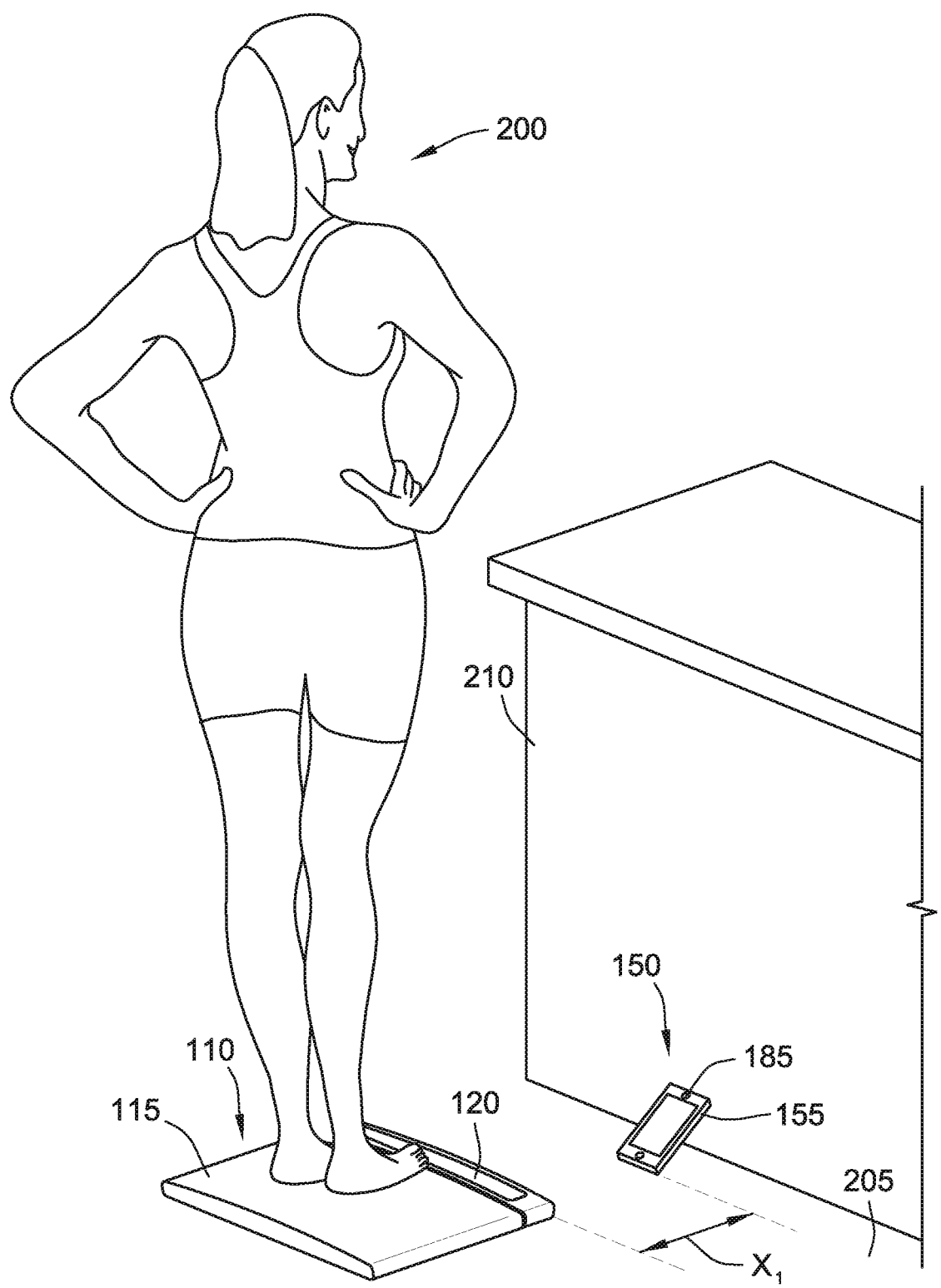
FIG. 2 is a perspective view of a user conducting a verified weigh-in using a weight verification system according to some implementations of the present disclosure.

Now referring to FIG. 2, a weight loss competition contestant or user 200 is shown conducting a verified weigh-in using the weight verification system 100. As shown, the user 200 is standing on the scale 110 with the housing 115 supporting the weight of the user 200 thereon. The mobile electronic device 150 is resting on a floor 205 (also supporting the scale 110) and leaning on a cabinet or wall 210 such that the front-facing camera 185 is generally aimed at the user 200 to capture a head-to-toe visual image and/or video of the user 200 during a verified weigh-in sequence. The server 190 is not shown as in this implementation the server 190 is offsite. The mobile electronic device 150 is shown as being placed a distance $X_1$ from the scale 110. The distance $X_1$ is between about six inches and about fifteen feet. Alternatively, the distance $X_1$ is between about two feet and eight feet. In some implementations, the distance $X_1$ is about six feet. The distance $X_1$ can be any number such that the front-facing camera 185 is able to capture the desired portion(s) of the user 200 (e.g., head-to-toe pictures, lower body only pictures, upper body only pictures, etc., or any combination thereof).

Figure 3:
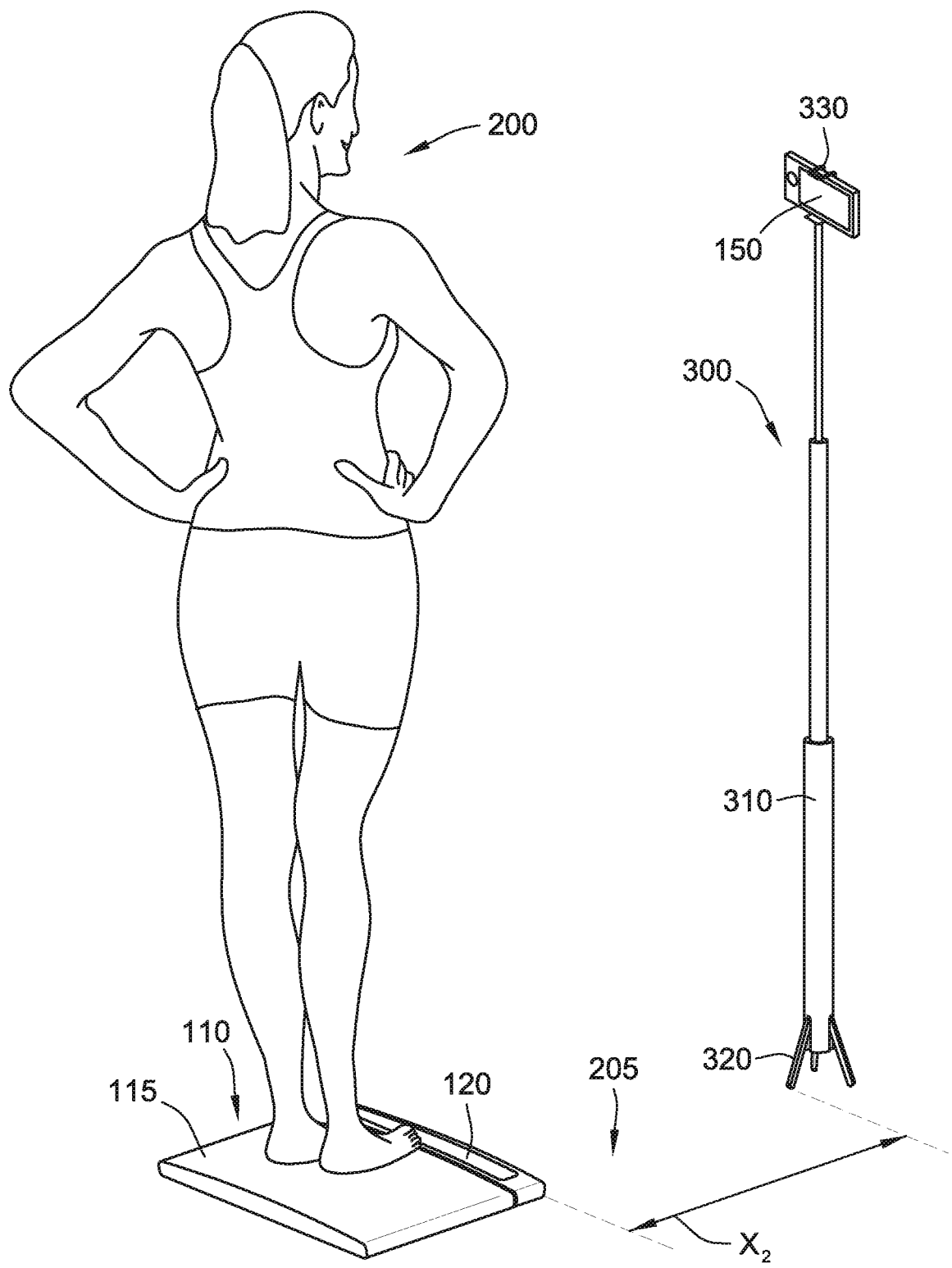
FIG. 3 is a perspective view of a user conducting a verified weigh-in using a weight verification system with a free-standing extendible member according to some implementations of the present disclosure.

Now referring to FIG. 3, the weight loss competition contestant or user 200 is shown conducting a verified weigh-in using the weight verification system 100 and a free-standing extendible member 300. The free-standing extendible member 300 (e.g., a tripod stand, a selfie-stick, or the like) includes a telescoping body 310, feet 320, and a coupling mechanism 330. The telescoping body 310 is able to extend from a collapsed-storage configuration (not shown) to a second extended configuration (shown in FIG. 3). The telescoping body 310 is adjustable to adjust the height of the free-standing extendible member 300 during its use. The feet 320 extend from the telescoping body 310 to provide support for the telescoping body 310 to remain substantially upright when placed on the floor 205. The coupling mechanism 330 is a universal coupling mechanism that is adjustable to securely hold therein, in a releasable fashion, a variety of sizes, types, makes, models, etc. of the mobile electronic device 150. The mobile electronic device 150 is shown as being placed a distance $X_2$ from the scale 110. The distance $X_2$ is between about six inches and about fifteen feet. Alternatively, the distance $X_2$ is between about two feet and eight feet. In some implementations, the distance $X_2$ is about six feet. The distance $X_2$ can be any number such that the front-facing camera 185 (or the rear-facing camera 185, not shown in FIG. 3) is able to capture the desired portion(s) of the user 200 (e.g., head-to-toe pictures, lower body only pictures, upper body only pictures, etc., or any combination thereof). While the telescoping body 310 is shown as having a generally circular cross-section, the telescoping body 310 can alternatively have a cross-section that is generally square, generally rectangular, generally triangular, generally oval, generally polygonal, or any combination thereof.

Now referring to FIGS. 4A and 4B, an alternative implementation of the scale 110 is shown where the housing 115 includes a cavity 400 therein that is sized and shaped to store the free-standing extendible member 300 in its collapsed-storage configuration. As shown, in the collapsed-storage configuration, the feet 320 are retracted from their extended position (FIG. 3) to further compact the free-standing extendible member 300 for storage.

Now referring to FIGS. 5A-5D, an alternative implementation of the scale 110 is shown as scale 510 for use by itself and/or within the weight verification system 100 as described herein. The scale 510 includes a main housing 515a and a movable housing 515b coupled to the main housing 515a via a pair of rods 518 (shown in FIGS. 5C and 5D). The rods 518 permit the movable housing 515b to move between a first retracted position (FIGS. 5A and 5B) and a second extended position (FIGS. 5C and 5D) by sliding/rolling relative to the main housing 515a. The movable housing 515b includes a pair of rollers/wheels 519 that aid in the movable housing 515b moving between the retracted and extended positions. The rods 518 are shown as having a generally cylindrical shape with a generally circular cross-section; however, the rods 518 can have any type of cross-sectional shape, such as, for example, square, rectangular, triangular, polygonal, etc., or any combination thereof. While two rods 518 are shown, the scale 510 can have any number of rods 518 coupling the main and movable housings 515a,b (e.g., one rod, three rods, four rods, etc.).

Figure 5A:
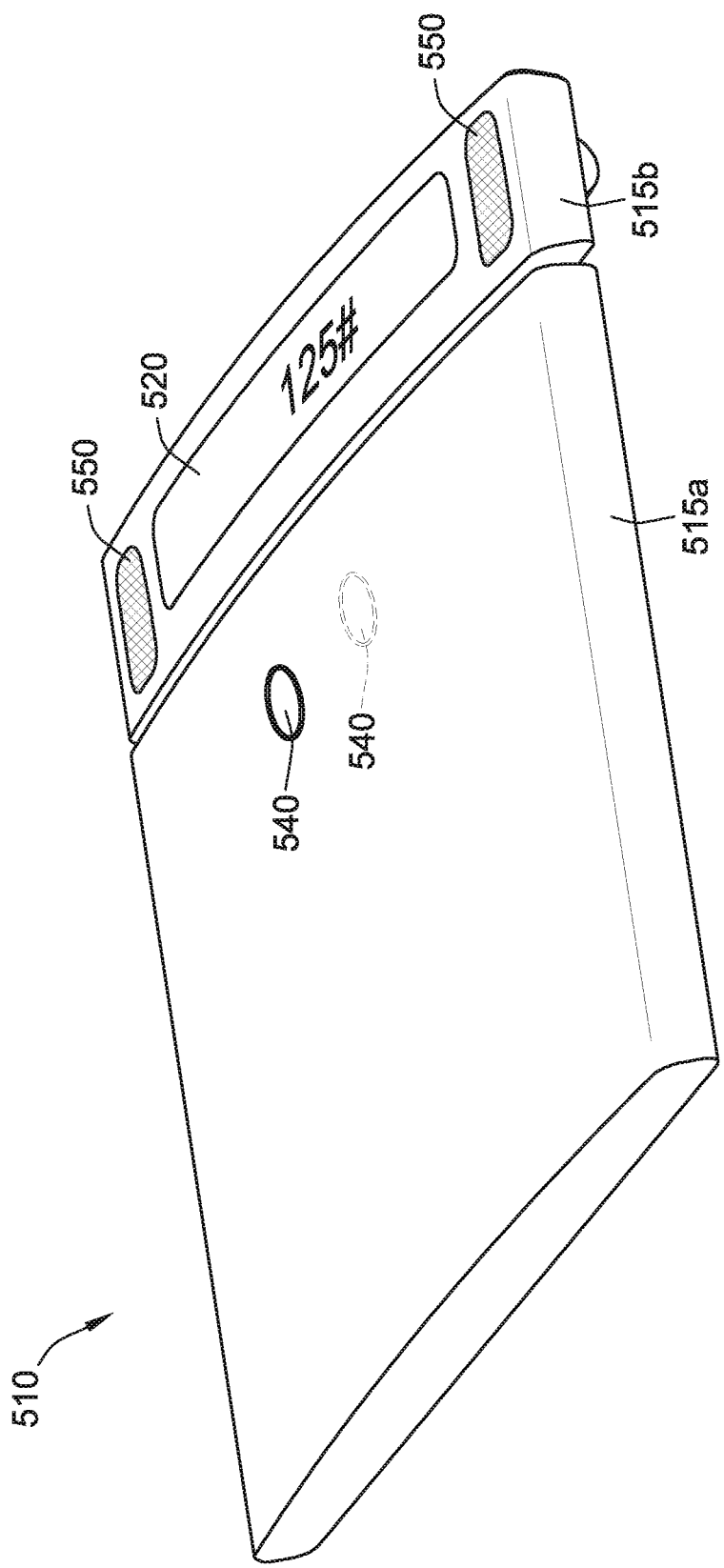
FIG. 5A is a top perspective view of a scale with a movable housing in a retracted position according to some implementations of the present disclosure.
Figure 5B:
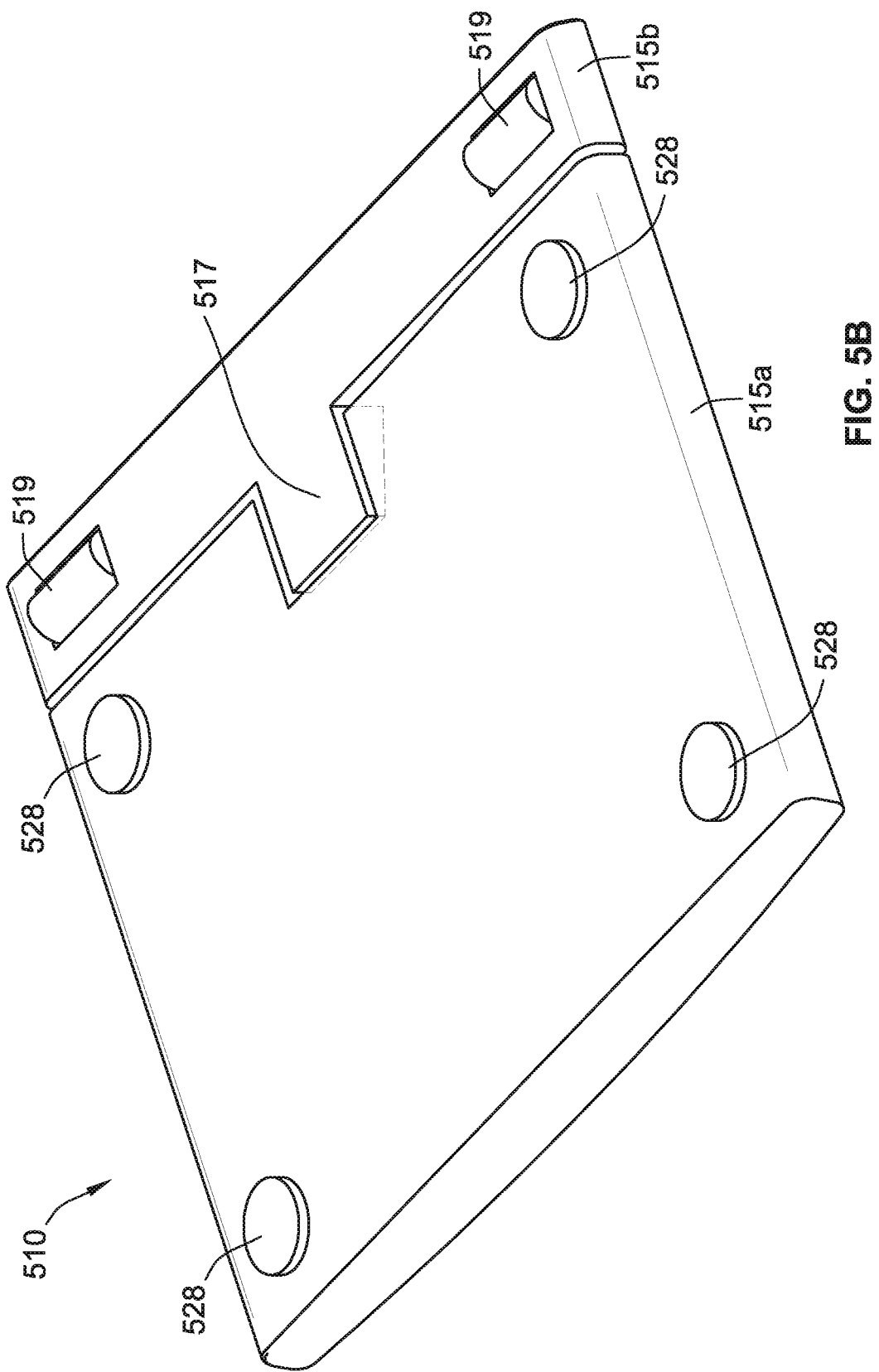
FIG. 5B is a bottom perspective view of the scale of FIG. 5A with the movable housing in the retracted position.
Figure 5C:
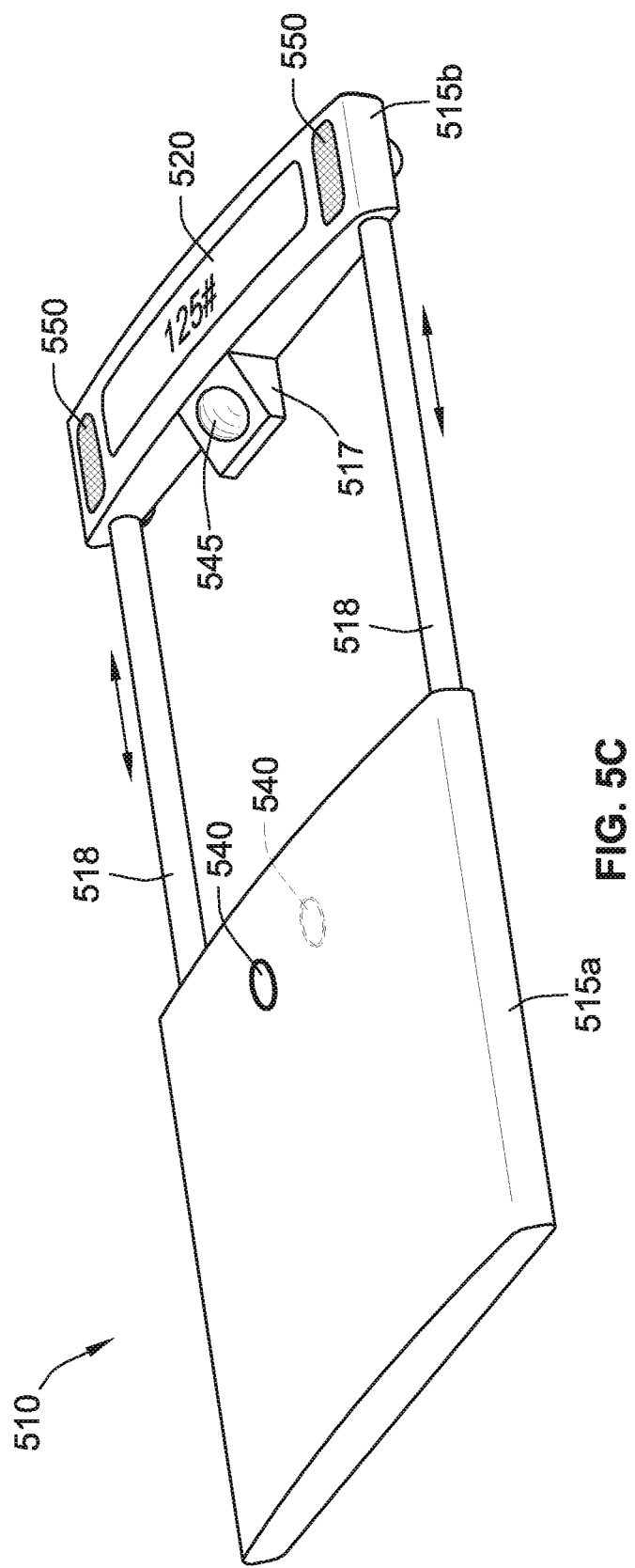
FIG. 5C is a top perspective view of the scale of FIG. 5A with the movable housing in an extended position.

The main and movable housings 515a,b can each have any shape or size and be made of any material, such as, for example, plastic, metal (e.g., aluminum, steel, titanium), rubber, or any combination thereof. As best shown in FIG. 5D, the main housing 515a includes a cutout/undercut or slot 516 that receives a protrusion 517 of the movable housing 515b therein when the movable housing 515b is in the first retracted position (FIGS. 5A and 5B). The protrusion 517 can also be referred to as a camera housing as the protrusion 517 includes at least a portion of a camera 545 therein (e.g., at least a lens of the camera 545 is included in and/or mounted to the protrusion 517). The camera 545 can be the same as, or similar to, the various cameras described herein. As shown, the camera 545 includes a fisheye lens for taking wide-angle pictures (e.g., the camera 545 is able to generate image data that is reproducible as a visual image and/or a visual video clip of at least a portion of a user supported on the main housing 515a of the scale 510), which can aid in capturing a relatively wider shot/picture as compared to a camera that does not have a fisheye lens (e.g., from the same distance from the object being captured in the picture). By positioning the camera 545 on/in the protrusion 517, the user of the scale 510 can selectively and physically cover/obscure the lens of the camera 545. Such a feature is especially advantageous when the scale 510 is placed in a bathroom as this obscuring feature can provide added comfort and peace of mind to the user that the lens of the camera 545 is not able to capture images of the user when not intended.

Similar to the scale 110, the scale 510 includes an electronic display 520 that is viewable and able to display a variety of information (e.g., the same information described herein). As shown, the electronic display 520 is coupled to the movable housing 515b; however, the electronic display 520 can alternatively be coupled to the main housing 515a. Additionally, two electronic displays 520 (not shown) can be included in the scale 510 such that one is coupled to the main housing 515a and the other is coupled to the movable housing 515b.

To aid in the main housing 515a remaining stationary when the movable housing 515b is moved into the extended position, the main housing 515a can include a number of feet 528. The feet 528 can be rubber, plastic, metal, or any combination thereof. The feet 528 protrude a distance from a bottom surface of the main housing 515a that is the same as, or very close to, the distance that the roller/wheels 519 protrude from the bottom surface of the movable housing 515b. Alternatively, the roller/wheels 519 protrude from the bottom surface of the movable housing 515b more or less (e.g., ±0.01 inches, ±0.05 inches, ±0.1 inches, ±0.2 inches, ±0.25 inches, etc.) than the feet 528 protrude from the bottom surface of the main housing 515a.

The scale 510 includes one or more toe-push buttons as input device(s) 540 of the scale 510. As shown, the toe-push-buttons 540 are relatively flush with (e.g., not recessed and not protruding from) an upper surface of the main housing 515a of the scale 510. Alternatively, the toe-push-buttons 540 can be recessed in or protruding from the upper surface of the main housing 515a of the scale 510. Generally, the toe-push-buttons 540 can be positioned in any fashion relative to the main housing 515a as long as the toe-push-button(s) 540 are readable accessible by the user of the scale 510 (e.g., using a toe or portion of a foot/feet) to be manually activated in the same, or similar, manner as the input device 140 described herein. As shown, two toe-push-buttons 540 are positioned side-by-side and spaced apart a distance (e.g., 0.5 inches, 1.0 inches, 1.5 inches, 2 inches, etc.) such that a first one of the toe-push-buttons 540 is generally positioned to be activated by a first toe (e.g., big toe) of a left foot of a user and a second one of the toe-push-buttons 540 is generally positioned to be activated by a first toe (e.g., big toe) of a right foot of the user at the same time or about the same time.

The movable housing 515b includes a pair of gripper 550 positioned adjacent to the left and right ends of the movable housing 515b. The grippers 550 can be used to aid a user in moving the movable housing 515b between the retracted and extended positions. The grippers 550 can be rubber, plastic, metal, or any combination thereof. The grippers 550 can have a surface pattern increases surface friction when engaged by the user to move the movable housing 515b between the retracted and extended positions.

While not shown in FIGS. 5A-5D, the scale 510 includes the same, or similar, components contained in the scale 110, such as, for example, a wireless communication module, a memory device storing instructions, one or more processors, one or more speakers, etc., or any combination thereof.

While the rods 518 are shown as being generally straight (e.g., having a linear central axis), the rods 518 can have a variety of other shapes. For example, in an alternative implementation, each of the pair of rods 518 is generally curved (e.g., C-shaped or the like) such that moving the movable housing 515b from the retracted position to the extended position causes the movable housing 515b to not only extend from the main housing 515a, but to also move vertically relative to the main housing 515a (e.g., the movable housing 515b move off of the floor holding the scale 510). In some such implementations, the curved rods (not shown) aid in providing a different angle for the camera 545 to capture pictures/videos/image data of the user on the main housing 515a.

Figure 6C:
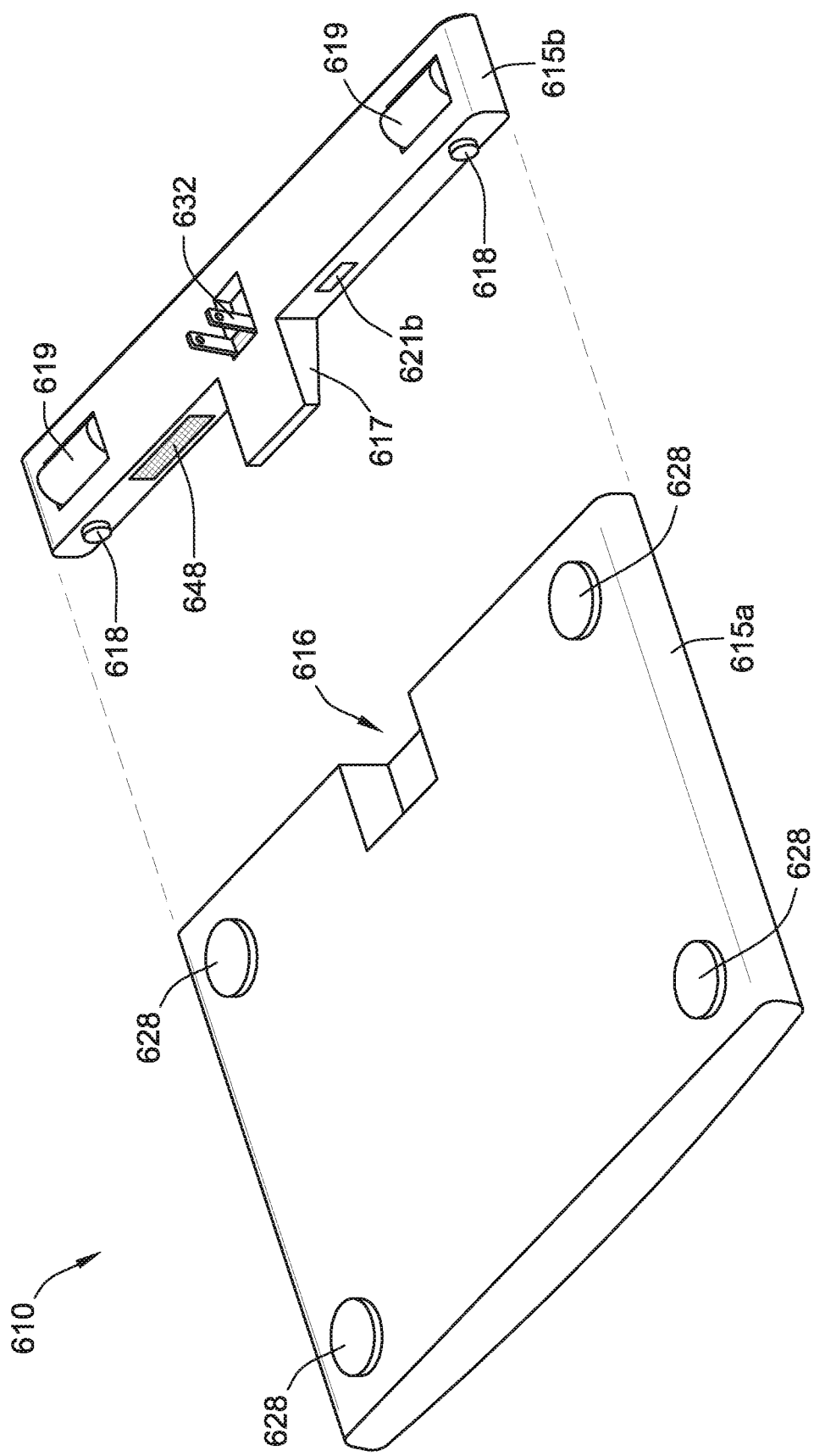
FIG. 6C is a bottom perspective view of the scale of FIG. 6B with the detachable housing detached from and spaced away from the main housing.

Now referring to FIGS. 6A-6C, an alternative scale 610 is shown for use by itself and/or within the weight verification system 100 as described herein. The scale 610 is similar to the scale 510 but mainly differs in that the scale 610 does not include the rods 518. The scale 610 includes a main housing 615a and a detachable housing 615b. Because the detachable housing 615b is not coupled to the main housing 615a via rods, the detachable housing 615b has relatively more freedom (as compared with the movable housing 515b) for its placement when conducting a verified weigh-in and taking pictures of the user on the main housing 615a.

The detachable housing 615b can be removably coupled to the main housing 615a via a coupling mechanism 618 (e.g., a magnetic latch or the like). The detachable housing 615b includes a pair of rollers/wheels 619 that aid in the detachable housing 615b moving or rolling along the floor (e.g., bathroom floor) supporting the scale 610 thereon.

The main and detachable housings 615a,b can each have any shape or size and be made of any material, such as, for example, plastic, metal (e.g., aluminum, steel, titanium), rubber, or any combination thereof. As best shown in FIG. 6C, the main housing 615a includes a cutout/undercut or slot 616 that receives a protrusion 617 of the detachable housing 615b therein when the detachable housing 615b is coupled to the main housing 615a via the coupling mechanism 618 (FIG. 6A). The protrusion 617 is the same as, or similar to, the protrusion 517 and includes at least a portion of a camera 645 therein (which is the same as, or similar to, the camera 545).

Similar to the scale 110, the scale 610 includes an electronic display 620 that is viewable and able to display a variety of information (e.g., the same information described herein). As shown, the electronic display 620 is coupled to the detachable housing 615b; however, the electronic display 620 can alternatively be coupled to the main housing 615a. Additionally, two electronic displays 620 (not shown) can be included in the scale 610 such that one is coupled to the main housing 615a and the other is coupled to the detachable housing 615b.

To aid in the main housing 615a remaining stationary when the detachable housing 615b is detached from and/or moved away from (e.g., spaced from) the main housing 615a, the main housing 615a can include a number of feet 628 that are the same as, or similar to, the feet 528. The detachable housing 615b includes a pair of gripper 650 that are the same as, or similar to, the grippers 550. The scale 610 can also include one or more speakers 648 that are the same as, or similar to, the speakers 148 described herein. While not shown in FIGS. 6A-6C, the scale 610 includes the same, or similar, components contained in the scale 110, such as, for example, a wireless communication module, a memory device storing instructions, and one or more processors, etc., or any combination thereof.

The scale 610 includes an electrical plug 632 for plugging the detachable housing 615b directly into an electrical outlet or the like for charging a power source (e.g., rechargeable battery) (not shown) contained within the detachable housing 615b. The power source can be used to power any of the electronic components (e.g., processor, memory, display, etc.) of the scale 610, whether the components are contained within the detachable housing 615b and/or in the main housing 615a. As shown, the main and detachable housings 615a,b include electrical power couplers 621a,b that electrically couple the main and detachable housings 615a,b together when the detachable housing 615b is coupled with the main housing 615a via the coupling mechanism 618. The electrical power couplers 621a,b permit power to be transferred from the power source in the detachable housing 615b to a second power source (e.g., rechargeable battery) (not shown) in the main housing 615a.

Figures 7A, 7B, 7C:
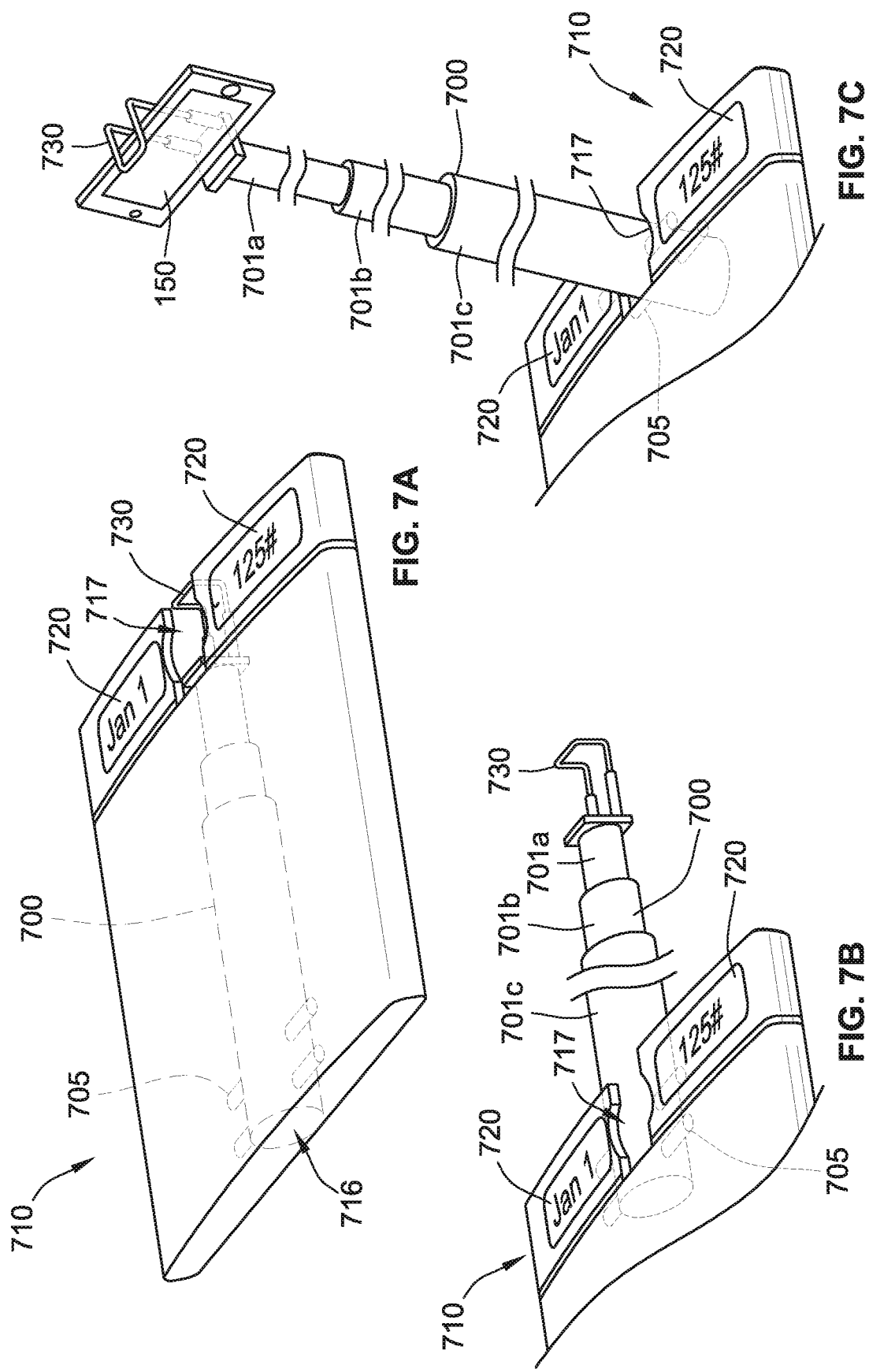
FIG. 7A is a perspective view of a scale with an extendible member stored in a housing of the scale in a collapsed-storage position according to some implementations of the present disclosure.
FIG. 7B is a partial perspective view of the scale of FIG. 7A with the extendible member extending from the housing of the scale in a collapsed and generally horizontal position.
FIG. 7C is a partial perspective view of the scale of FIG. 7A with the extendible member of the scale in an extended-generally-upright position and a coupling mechanism holding a mobile electronic device.

Now referring to FIGS. 7A-7G, an alternative scale 710 is shown for use by itself and/or within the weight verification system 100 as described herein. The scale 710 is similar to the scale 110 shown in FIGS. 4A and 4B but mainly differs in that the scale 710 includes an extendible member 700 that is coupled to a housing 715 of the scale 710 (e.g., as opposed to the free-standing extendible member 300 that is not coupled to the housing 115) such that the extendible member 700 is movable between a collapsed-storage position (FIGS. 7A and 7D) and an extended-generally-upright position (FIG. 7C).

The extendible member 700 includes a multitude of telescoping parts 701a-c such that the extendible member 700 is extendible from its collapsed configuration (FIGS. 7A and 7E-7G) to an extended configuration (FIG. 7C). When the extendible member 700 is fully collapsed (FIG. 7A), the extendible member 700 has a first length and when the extendible member 700 is fully extended (FIG. 7C), the extendible member 700 has a second length that is greater than the first length. For example, the second length is about two times the first length. For another example, the second length is about three times the first length. For another example, the first length is about one foot and the second length is about three feet. Various other lengths are contemplated for the extendible member 700 in the collapsed and extended configurations. While the extendible member 700 is shown as having the telescoping parts 701*a-c* with a generally circular cross-sectional shape, the telescoping parts 701*a-c* can have any shaped cross-section, such as, for example, generally square, generally rectangular, generally triangular, generally oval, generally polygonal, or any combination thereof. The telescoping parts 701*a-c* can remain in the extended position automatically and/or by engaging a locking mechanism (not shown).

The extendible member 700 includes a coupling mechanism 730 that extends from a top or first end of the extendible member 700. The coupling mechanism 730 is the same as, or similar to, the coupling mechanism 330 in that the coupling mechanism 730 is a universal coupling mechanism that is adjustable to securely hold therein, in a releasable fashion, a variety of sizes, types, makes, models, etc. of the mobile electronic device 150 (FIG. 7C).

The extendible member 700 includes a pivotable-pin assembly 705 that extends from a bottom or second end of the extendible member 700. The pivotable-pin assembly 705 includes four pins protruding from the second end of the extendible member 700. Two of the four pins extend along a first axis that is generally perpendicular to a central axis of the extendible member 700 and the other two of the four pins extends along a second axis that is parallel to the first axis and generally perpendicular to the central axis of the extendible member 700. The pivotable-pin assembly 705 is designed and positioned to engage a track 735 (FIGS. 7D-7G) of the scale 710 in a slidable and/or pivotable fashion as described below.

The housing 715 of the scale 710 includes a cavity 716 for storing the extendible member 700 therein when not in use (e.g., when not conducting a verified weigh-in). The housing 715 of the scale 710 also includes a cutout or notch 717 for accommodating a portion of the extendible member 700 when the extendible member 700 is in the extended-generally-upright position (FIG. 7C). The housing 715 and/or the cavity 716 form the track 735 along which the pivotable-pin assembly 705 slides and/or pivots. For example, in some implementations, the pivotable-pin assembly 705 operatively engages the track 735 such that the extendible member 700 is able to slide relative to the housing 715 from the collapsed-storage position (FIGS. 7A and 7D) to a collapsed and generally horizontal position (FIGS. 7B and 7E). After reaching the collapsed and generally horizontal position (FIGS. 7B and 7E), the pivotable-pin assembly 705 is further able to pivot relative to the housing 715 within the track 735 into a first intermediate position (FIG. 7F) and then the pivotable-pin assembly 705 drops downward slightly relative to the housing 715 within the track 735 into a second position (FIG. 7G) where the extendible member 700 is in a collapsed-generally-upright position. Once in the collapsed-generally-upright position, the extendible member 700 can be extended into the extended-generally-upright position (FIG. 7C).

The angle of the extendible member 700 relative to horizontal is determined by the portion of the track 735 engaging the pivotable-pin assembly 705 when the extendible member 700 is in a collapsed-generally-upright position. As such, the angle can vary depending on the design and orientation of the track 735. In some implementations, the angle of the extendible member 700 relative to horizontal in the collapsed-generally-upright position (and/or in the extended-generally-upright position shown in FIG. 7C) is between about thirty degrees and about ninety degrees. In some other implementations, the angle of the extendible member 700 relative to horizontal in the collapsed-generally-upright position (and/or in the extended-generally-upright position shown in FIG. 7C) is between about forty-five degrees and ninety degrees. In yet some other implementations, the angle of the extendible member 700 relative to horizontal in the collapsed-generally-upright position (and/or in the extended-generally-upright position shown in FIG. 7C) is between about fifty-five degrees and about seventy degrees. In yet some other implementations, the angle of the extendible member 700 relative to horizontal in the collapsed-generally-upright position (and/or in the extended-generally-upright position shown in FIG. 7C) is between about zero degrees and about one hundred and eighty degrees. Various other angles of the extendible member 700 relative to horizontal are contemplated, such as, for example, about five degrees, about ten degrees, about fifteen degrees. In some of such implementations, the extendible member 700 may further include a leg (not shown) that extends outward from the extendible member 700 in the extended-generally-upright position and rests on and/or engages the floor to aid in supporting the weight of the extendible member 700 itself (and/or any item(s) coupled thereto, like a mobile electronic device).

The scale 710 includes two electronic displays 720 that are viewable and able to display a variety of information (e.g., the same information described herein). As shown, the two electronic displays 720 are coupled to the housing 715 on opposite sides of the notch 717. However, in some alternative implementations, the notch 717 and/or the electronic displays 720 are moved such that the two electronic displays 720 are a single electronic display (not shown) coupled to the housing 715.

To aid in preventing the housing 715 from tipping over when the extendible member 700 is in the extended-generally-upright position (FIG. 7C) and/or coupled with the mobile electronic device 150 (e.g., when a user is not standing on the housing 715), one or more counter-weights (not shown) can be positioned within the housing 715. For example, a counter-weight(s) may be positioned within the housing 715 in the end opposite the end of the notch 717 and/or the electronic displays 720. The scale 710 can also include a number of feet 728 (the same as, or similar to, the feet 528).

While not shown in FIGS. 7A-7G, the scale 710 includes the same, or similar, components contained in the scale 110, such as, for example, a wireless communication module, a memory device storing instructions, one or more processors, one or more speakers, one or more input devices (e.g., toe-push buttons), etc., or any combination thereof.

Figure 8:
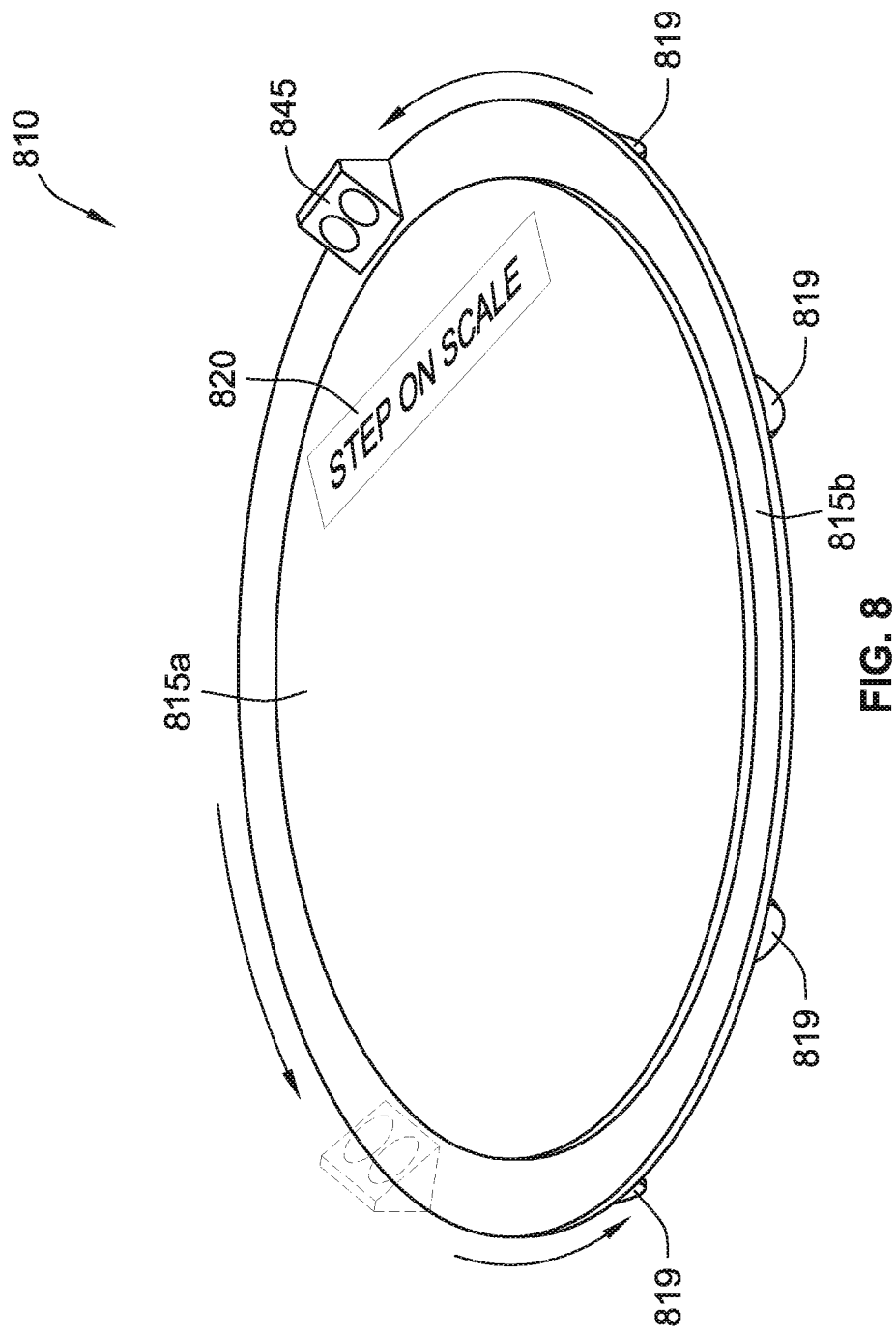
FIG. 8 is a perspective view of a scale with a rotating housing according to some implementations of the present disclosure.

Now referring to FIG. 8, an alternative scale 810 is shown for use by itself and/or within the weight verification system 100 as described herein. The scale 810 includes a main housing 815*a*, a rotating housing 815*b*, an electronic display 820, and a camera 845. The rotating housing 815*b* generally has a ring shape and is positioned around the main housing 815*a* and operatively coupled thereto via a drive system (not shown) that is able to cause the rotating housing 815*b* to rotate about the main housing 815*a* in a clockwise and/or counterclockwise direction. The camera 845 is mounted to the rotating housing 815*b* such that rotation of the rotating housing 815*b* causes the camera 845 to rotate. As such, the camera 845 is able to capture a 360 degree view (e.g., a body scan or body image) of a user standing on the main housing 815*a*. In some implementations, the camera 845 includes a fisheye lens, a flash, dual lenses, etc., or any combination thereof.

The rotating housing 815*b* can include a multitude of roller/wheels 819 that aid in the rotating housing 815*b* moving/rotating about the main housing 815*a*. To aid in the main housing 815a remaining stationary when the rotating housing 815b is moving/rotating, the main housing 815a can include a number of feet (not shown) that are the same as, or similar to, the feet 528.

The scale 810 includes the electronic display 820 that is viewable and able to display a variety of information (e.g., the same information described herein). While not shown, a second electronic display can be included and coupled to the rotating housing 815b.

While not shown in FIG. 8, the scale 810 includes the same, or similar, components contained in the scale 110, such as, for example, a wireless communication module, a memory device storing instructions, one or more processors, one or more speakers, etc., or any combination thereof.

Figure 9:
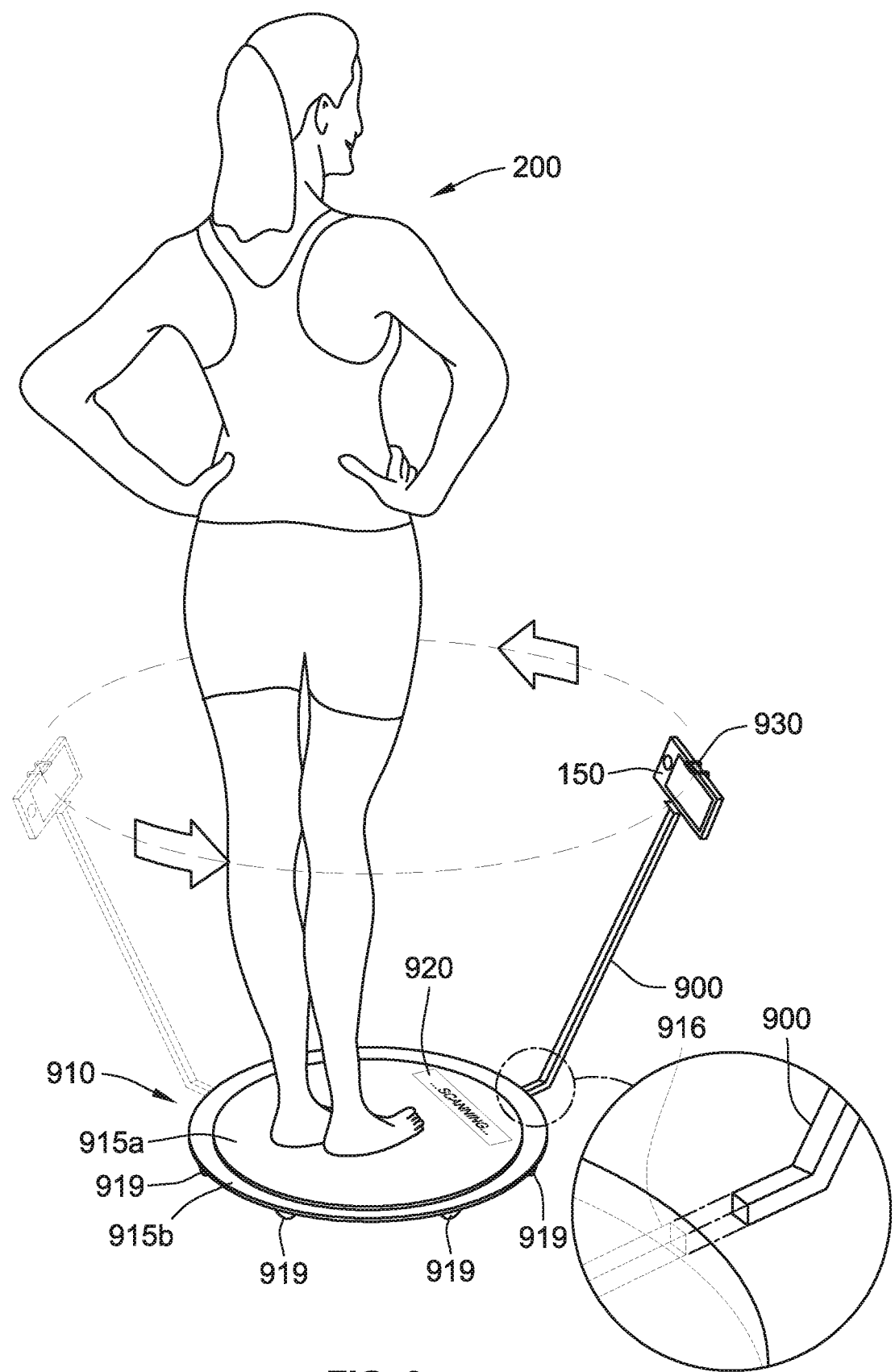
FIG. 9 is a perspective view of a scale with a rotating housing coupled to a removably attachable rod member according to some implementations of the present disclosure.

Now referring to FIG. 9, an alternative scale 910 is shown for use by itself and/or within the weight verification system 100 as described herein. The scale 910 is similar to the scale 810 but mainly differs in that instead of the scale 910 including a built-in camera, the scale 910 includes a removably attachable rod member 900 with a coupling mechanism 930 that is coupled to a rotating housing 915b of the scale 910. The coupling mechanism 930 is the same as, or similar to, the coupling mechanism 330 in that the coupling mechanism 930 is a universal coupling mechanism that is adjustable to securely hold therein, in a releasable fashion, a variety of sizes, types, makes, models, etc. of the mobile electronic device 150.

The scale 910 includes a main housing 915a, the rotating housing 915b, an electronic display 920, and the removably attachable rod member 900. The rotating housing 915b generally has a ring shape and is positioned around the main housing 915a and operatively coupled thereto via a drive system (not shown) that is able to cause the rotating housing 915b to rotate about the main housing 915a in a clockwise and/or counterclockwise direction. The rotating housing 915b includes a slot 916 that receives a portion of the removably attachable rod member 900 therein, thereby coupling the removably attachable rod member 900 with the rotating housing 915b. The mobile electronic device 150 is held by the coupling mechanism 930 of the removably attachable rod member 900, which is mounted to the rotating housing 915b, such that rotation of the rotating housing 915b causes the mobile electronic device 150 to rotate. As such, a camera of the mobile electronic device 150 is able to capture a 360 degree view (e.g., a body scan or body image) of the user 200 standing on the main housing 915a.

The rotating housing 915b can include a multitude of roller/wheels 919 that aid in the rotating housing 915b moving/rotating about the main housing 915a. To aid in the main housing 915a remaining stationary when the rotating housing 915b is moving/rotating, the main housing 915a can include a number of feet (not shown) that are the same as, or similar to, the feet 528.

The scale 910 includes the electronic display 920 that is viewable and able to display a variety of information (e.g., the same information described herein). While not shown, a second electronic display can be included and coupled to the rotating housing 915b.

While not shown in FIG. 9, the scale 910 includes the same, or similar, components contained in the scale 110, such as, for example, a wireless communication module, a memory device storing instructions, one or more processors, one or more speakers, etc., or any combination thereof.

While the removably attachable rod member 900 is shown as being a rigid member, the removably attachable rod member 900 can be replaced with a collapsible and/or extendable removably attachable rod member that is similar to the extendible member 700 and/or the free-standing extendible member 300).

Several of the scales of the present disclosure include built-in cameras. To aid the users in determining whether the cameras are on/live (e.g., recording images), one or more alert systems can be included in any of the scales and/or mobile electronic devices of the present disclosure. For example, a light ring can be placed around the lens of the camera that glows a first color (e.g., red) when the camera is on and glows a second color (e.g., green) when the camera is off.

Figure 10B:
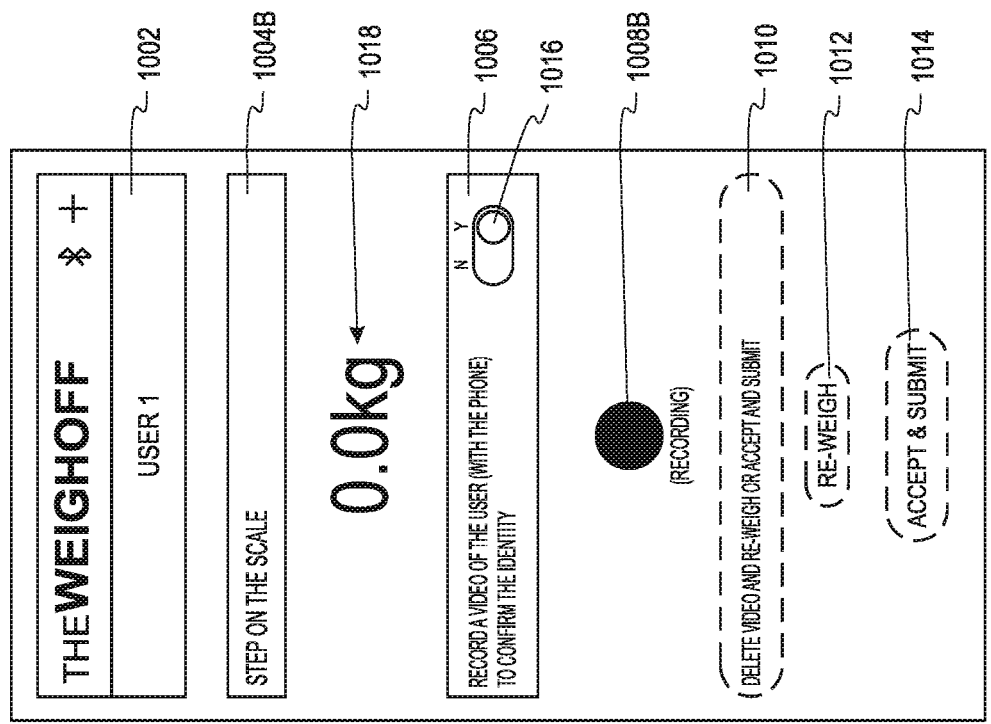
FIG. 10B is a front view of a user interface at a second time during a verified weight sequence.
Figure 10A:
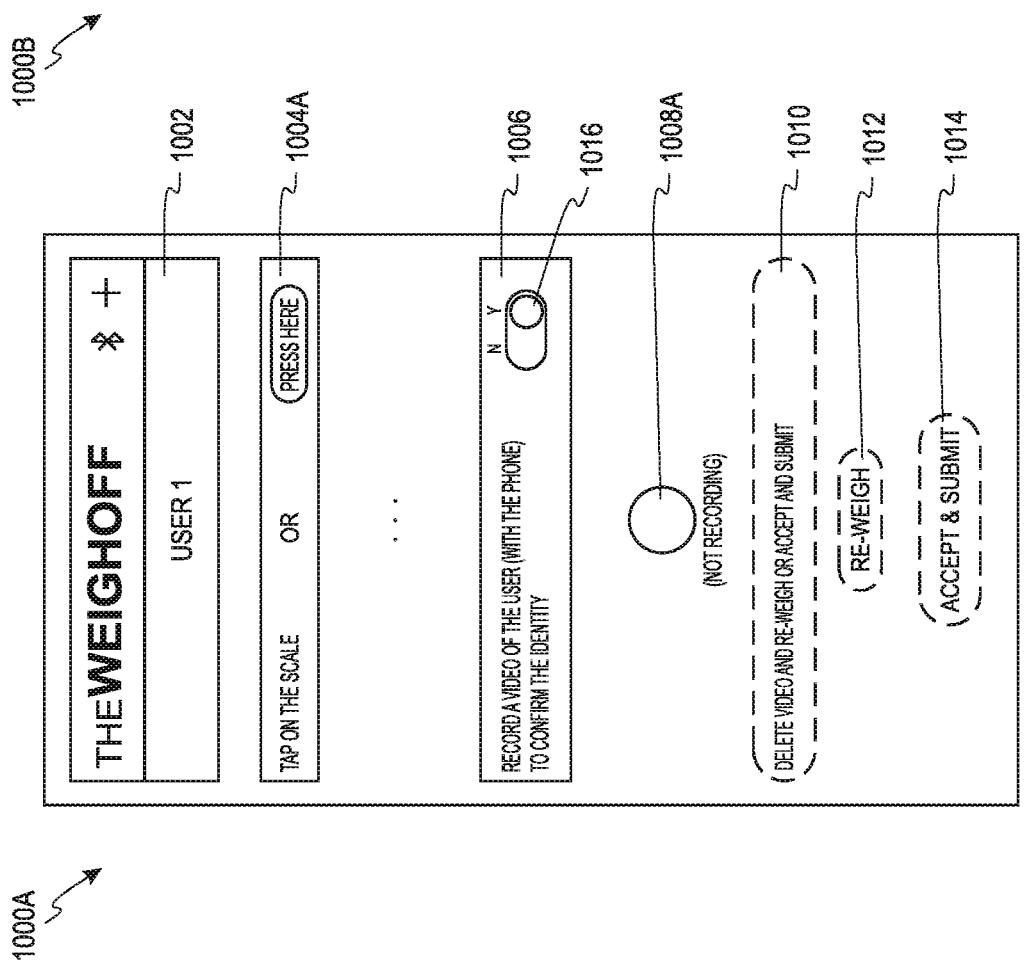
FIG. 10A is a front view of a user interface at a first time during a verified weight sequence.

Now referring generally to FIGS. 10A-10D, a user interface 1000 of mobile electronic device 150 is illustrated. FIG. 10A illustrates user interface 1000A prior to a user stepping onto the scale. User interface 1000 of FIGS. 10A-10D is operable with any of the scales discussed in the present disclosures, including scale 110, 510, 610, 710, 810, or 910. User interface 1000A may include a user indicator 1002, a text area 1004A, a record video option 1006, and a recording indicator 1008A. User interface 1000A may also include post-weigh in information area 1010, as well as user-selectable options 1012 and 1014. User-selectable option 1012 allows the user to re-weigh himself or herself, while user selectable option 1014 allows a user to accept and submit a weigh in. Both user-selectable options 1012, 1014 may at various times be grayed out or blank (or simply missing from the display) and thus may not be selectable by the user at certain times, as indicated by the dashed lines in FIG. 10A. Post-weigh in information area 1010 indicates information to the user after the user has completed the weigh-in procedure. Like user-selectable options 1012 and 1014, post-weigh in information area 1010 may be blank or may be grayed out, as indicated by the dashed lines.

User indicator 1002 indicates the identity of the user currently using the scale and mobile electronic device 150. User indicator 1002 may indicate the identity of the current user simply by displaying "User 1," "User 2," etc. User indicator 1002 may also indicate the identity of the current user by displaying the user's name, nickname, or some other type of identification. Text area 1004 may include instructions displayed to the user to command the user to take an action. In FIG. 10A, text area 1004A indicates to the user how to start the weigh-in procedure. As indicated in FIG. 10A, the user may start the weigh-in procedure by tapping on the scale or by selecting the "PRESS HERE" button. Record video option 1006 allows the user to select whether they would like a video record of themself during the weigh in to be recorded. The user may select whether or not to record a video by moving slider 1016 to either "N," indicating that a video should not be recorded, or to "Y," indicating that a video should be recorded. Finally, recording indicator 1008A can include an area that displays a blank circle or an outline of a circle when the mobile electronic device 150 is not currently recording, and/or text that states that mobile electronic device 150 is not recording. In some implementations, the user must permit the recording of the weigh in session to participate in a weight loss competition contest.

Now referring to FIG. 10B, user interface 1000B is illustrated that reflects the state of mobile electronic device 150 when the user has begun recording a video but has not yet stepped on the scale. Text area 1004B displays text instructing the user to step onto the scale. Recording indicator 1008B displays a shaded-in or solid circle, as well as text that indicates to the user that a video is currently being recorded. As shown, post-weigh in information area 1010 and user-selectable options 1012 and 1014 are still blank or grayed out. User interface 1000B also includes weight indicator 1018, which indicates to the user the weight sensed by the scale. As user interface 1000B is shown before the user steps onto the scale, weight indicator 1018 indicates that the scale is not currently sensing any weight.

Now referring to FIG. 10C, user interface 1000C is illustrated. Here, the user has stepped onto the scale, which is currently measuring the user's weight. As shown, text area 1004C displays text indicating to the user that the scale is currently measuring the user's weight, and that a video is being recorded. Weight indicator 1018 currently shows three dots, indicating that the scale is sensing that the user has stepped onto the scale (e.g., scale 110, 510, 610, 710, 810, 910) and that the scale is determining the user's weight. Weight indicator 1018 may display any suitable object, text, etc., to communicate that the scale is in the process of determining the user's weight after having sensed that the user has stepped onto the scale. Recording indicator 1008C may be overlaid on the top of a real-time video image 1020 of the user during the weigh-in. Real-time video image 1020 may show a continuous video of the weigh-in process, or may display a constantly updating series of still images. Real-time video image 1020 could also display a single still image captured at a point during the weigh-in process. Post-weigh in information area 1010 and user-selectable options 1012 and 1014 are still blank or grayed out.

Now referring to FIG. 10D, user interface 1000D is shown after the user has completed the weigh-in. Text area 1004D may display the word "WEIGHT," indicating that user interface 1000D is now displaying the measured weight. Weight indicator 1018 now displays the user's measured weight. Recording indicator 1008D indicates that the video recording has been completed and that no video is currently being recorded. Recording indicator 1008D also indicates that a video that may be played, by taking the form of a play button, i.e. a sideways-pointing triangle. Recording indicator 1008D is responsive to user input, for example the user manually pressing recording indicator 1008D when it appears on a touchscreen of mobile electronic device 150. Recording indicator 1008D is now overlaid on top of still frame 1022, which generally displays a still frame from the recorded video. When the user manually presses on recording indicator 1008D, still frame 1022 transforms into the recorded video, which is then played for the user. In general, the recorded video will include an image or images or video showing the user stepping onto the scale, the user standing on the scale when the scale determines the user's weight, and the user stepping off of the scale. In user interface 1000D, post-weigh in information area 1010 and user-selectable options 1012 and 1014 are no longer grayed out or blank. Post-weigh in information area 1010 now indicates to the user that the user can either delete the video and re-weigh himself or herself, or that the user can accept the weigh-in and submit the video (e.g., to be verified). User-selectable option 1012 is operable to accept user input to re-weigh the user. User-selectable option 1014 is operable to accept the result of the weigh-in and submit the video.

Figure 11:
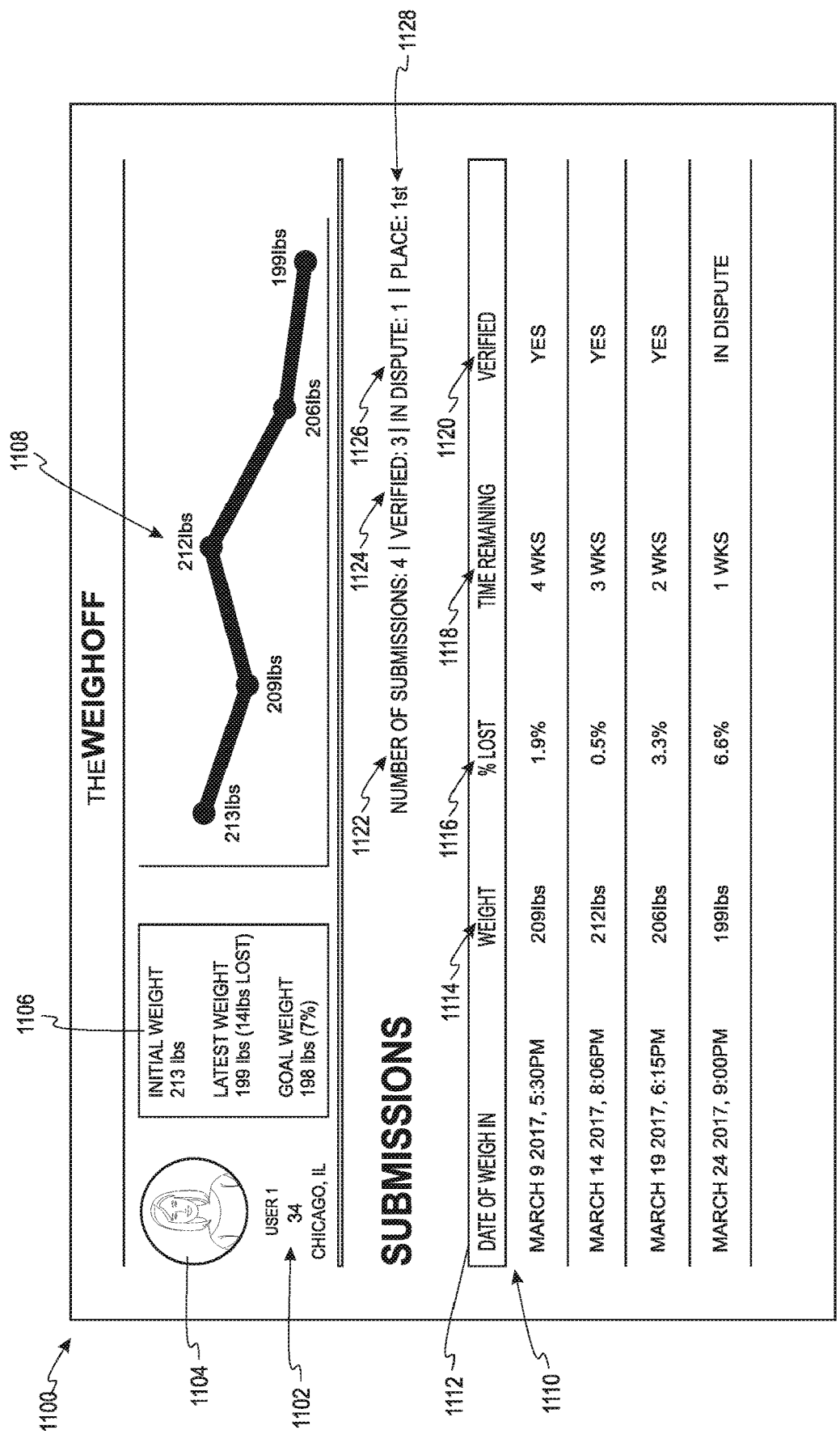
FIG. 11 is a front view of a user profile accessible by a user.

Referring now to FIG. 11, a user profile 1100 is illustrated. User profile 1100 may include personal user information 1102, a user profile image 1104, and contest weight information 1106. Personal user information 1102 may include the user's name, age, and location. Contest weight information 1106 may include the user's initial weight, the user's most recent weight, and indication of the difference between the user's most recent weight and the user's initial weight, the user's goal weight, and an indication of the difference between the user's goal weight and the user's initial weight. The indication of the difference between the user's most recent weight and the user's goal weight may take the form of a number of pounds lost, or a percentage. Similarly, the indication of the difference between the user's goal weight and the user's initial weight may take the form of a number of pounds or a percentage.

User profile 1100 also includes a weight graph 1108 which provides a visual indicator of the results of the user's submissions. For example, weight graph 1108 plots the recorded weights for each of the user's submissions to the contest and provides a line between each recorded weight, thus providing information on how the user has progressed during the contest. User profile 1100 further includes a weigh-in submission chart 1110, which shows details on each weigh-in submitted by the user. Each entry in weigh-in submission chart 1110 may include date and time 1112, the user's weight 1114, a percentage of weight lost 1116, the time remaining in the contest 1118, and a determination 1120 of whether the weigh-in was verified. The percentage of weight lost 1116 may be a percentage of the user's initial weight that the user has lost, or a percentage of the user's most recent weigh-in that they have lost. Weigh-in submission chart 1110 may also include information indicating a total number of submissions 1122, a number of verified submissions 1124, a number of in dispute weigh-ins 1126, and what place in the contest the user is currently in 1128.

Figure 12:
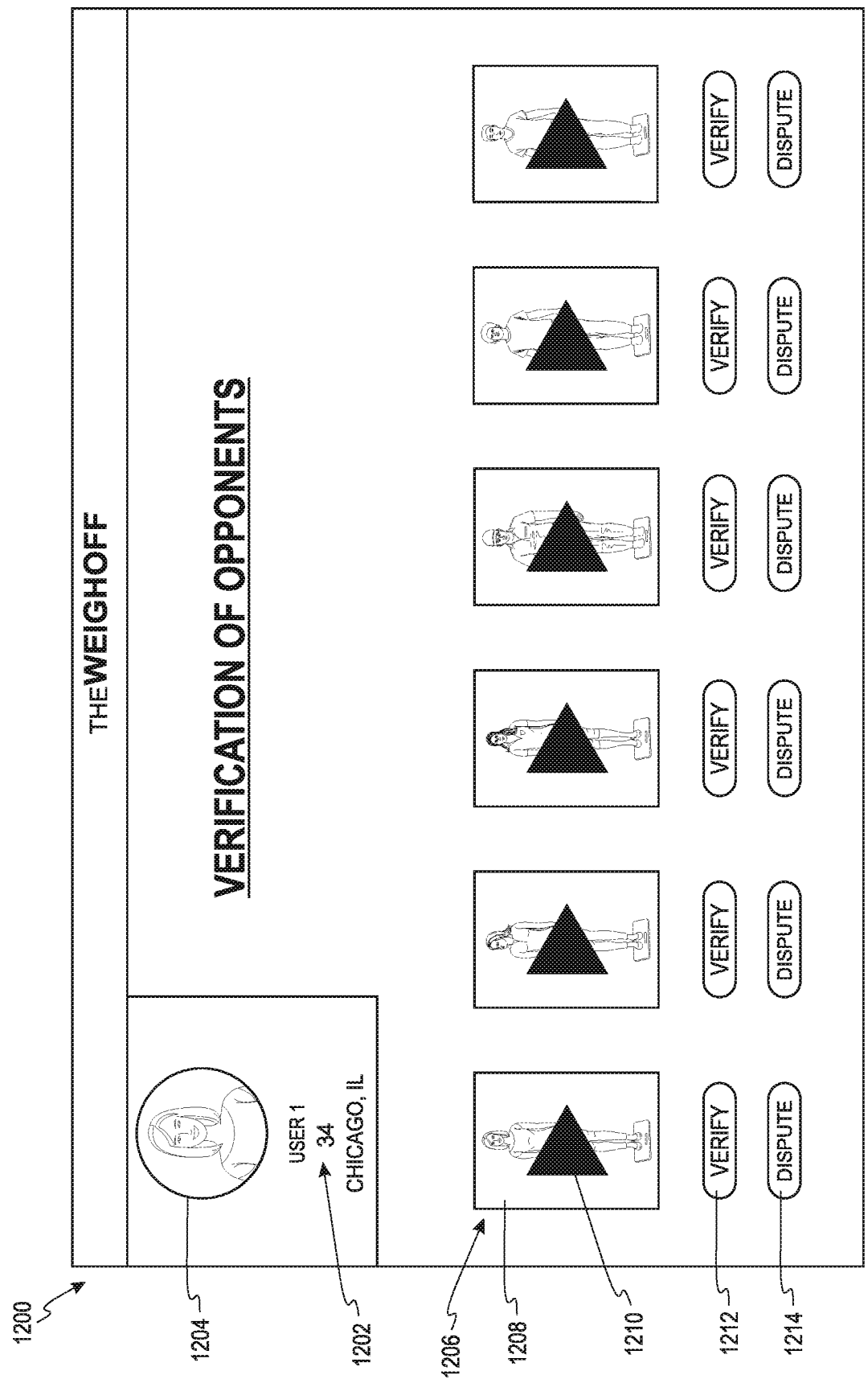
FIG. 12 is a front view of a verification screen where a user can view submitted weigh-in videos and verify or dispute the submitted weigh-in videos.

Now referring to FIG. 12, a verification screen 1200 is illustrated. Verification screen 1200 may be accessed by a user in a contest to review image data submitted by other contestants and either verify or dispute those weigh-ins. Verification screen 1200 may include personal user information 1202 such the user's name, the user's age, and the user's location, as well as a user profile image 1204. Verification screen 1200 also includes one or more verification areas 1206. Each verification area 1206 includes the image data 1208 of another user's weigh-in, a user-selectable play button 1210, a user-selectable "Verify" button 1212, and a user-selectable "Dispute" button 1214. Image data 1208 is generally uploaded and stored as a visually readable image or video of the user such that the user is personally identifiable by the visually readable image or video. The image data that is stored is not an avatar or other digital re-creations of the user, which can cause difficulties in verifying the submitted weigh-in. Avatars or other digital recreations/representations of users generally remove much of the context from the weigh-in videos, such that specific identifying aspects of the user are replaced by generic features on a digital human. As such, avatars do not produce video images that other users can verify by viewing them, as the other users have no way to determine whether the person who submitted the weigh-in is actually the contest user. For example, a contestant's sibling or friend that has a similar body shape could step in for the contestant's weigh in without the other contestants knowing if avatar representations of the contestants were used, which would not be suitable to a contest requiring verification of weigh ins.

The user may view the image data 1208 submitted by other users by pressing the play button 1210. The user then determines whether there is any reason to dispute the other users' weigh-ins. The use. The recorded weight for each submission may be displayed on verification screen 1200 (e.g., overlaid thereon and/or baked into the video) simultaneously with the recorded video of the weigh-in to allow a user to view both the weigh-in video and the recorded weight to help determine whether the weigh-in is legitimate and if it should be verified. The user may then verify the weigh-in by pressing the "Verify" button 1212. The user may also dispute the weigh-in by pressing the "Dispute" button 1214. The image data 1208 may be manually or automatically clipped or trimmed based on the time the user stepped onto the scale. For example, when a user plays a weigh-in video submitted by another user, the image data 1208 may begin playing at the moment the user stepped on the scale, even if that user's equipment captured video of the user at an earlier point before they stepped onto the scale. For another example, when a user plays a weigh-in video submitted by another user, the image data 1208 may begin playing at a predefined time prior the moment the user stepped on the scale (e.g., one, two, three, etc. seconds prior to stepping onto the scale).

In general, all weigh-ins submitted by a user are viewable by all other users in the weight loss competition and/or third party referees/judges. Submitted weigh-ins may be tagged and categorized by the method used to verify the submission. If a particular submission is disputed, a third party (such as a referee, judge, doctor, nurse, health or fitness instruction, designated user in the contest, etc.) may be utilized to administer a replacement weigh-in at an independent location. There may also be varying standards to trigger a dispute. In one implementation, a single user disputing a submitted weigh-in may trigger follow-up procedures to either determine whether the submitted weigh-in is legitimate or conduct a replacement weigh-in. In another embodiment, a predetermined percentage or number of users are required to dispute a submitted weigh-in to trigger the follow-up procedures. Similarly, a pre-determined percentage or number or users verifying a submitted weigh-in may automatically verify the submission, regardless of how many other users dispute the submitted weigh-in.

Other methods of verifying the use-submitted weigh-ins are also contemplated. For example, certified instructors or health professionals (e.g., referees/judges) may view the videos and verify the weigh-ins. Other vetted individuals may also conduct weigh-ins. For example, a user's personal health instructor could conduct a weigh-in publicly at their place of business while recording the weigh-in according to aspects of the present disclosure. Health professionals may also be able to view weigh-in videos and add notes to the videos. A representative or hired agent of the entity or person operating the weight loss contest may also administer the weigh-ins and verify weigh-in videos. Users may also be able to schedule weigh-ins with the weight loss contest operator so that the user and the contest operator can participate in a video conference during the weigh-in to record the weigh-in and monitor the weigh-in process. Weight verification system 100 may also include fingerprint detection functionality to verify the identity of the user. For example, mobile electronic device 150 may include a fingerprint reader that the user presses while stepping on to the scale. The scale may also include footprint technology to verify the identity of the user based on the user's footprint. The scale may also be capable of measuring a user's body fat percentage and pairing that measurement with the user's recorded weight. Monitoring the progress of the user's recorded weight and the user's measured body fat percentage can also assist in verifying the user's submitted weigh-in. Weight verification system 100 may also utilize facial recognition software or body recognition software to assist other users in verifying submitted weigh-ins, or to digitally verify weigh-ins. For example, weight verification system 100 can create a first user appearance profile at the time of a first weigh-in that includes a first user face profile and a first user body profile by utilizing facial recognition software and body recognition software. Before a second weigh-in, an expected user appearance profile can be created based on at least one of the first user appearance profile, the weight of the user recorded during the first weigh-in, and the time difference between the first weigh-in and the second weigh-in. A second user appearance profile is then created during the second weigh-in and is compared to the expected user appearance profile. This comparison can be utilized by other users to assist them in determining whether to dispute a given weigh-in submission. The comparison can also be used by weight verification system 100 to digitally determine whether to verify or dispute a weigh-in submission. For example, if the measured face and body appearance varies from the expected face and body appearance by a pre-determined amount, weight verification system 100 may automatically dispute a weigh-in submission.

A variety of follow-up procedures are available once a dispute has been triggered. The user may simply be asked to submit a new weigh-in video and result. Other users or weight verification system 100 may indicate to the user of the disputed submission what their concerns were so that if a simple mistake has been made during the weigh-in procedure, the user can correct for it. The user may be required to undergo a weigh-in conducted under the supervision of a health professional, a representative of the contest operator, or some other third party. The user may be required to undergo a weigh-in that is broadcast live to other users, to a health professional, to a representative of the contest operator, or to some other third party.

Weight verification system 100 can present results to the user in an easily accessible manner. Weight verification system 100 can organize the data into charts or graphs, and can provide guides or tips to the user based on the recorded data. Weight verification system 100 can also measure and monitor muscle mass and strength, for example to monitor arm muscle growth, chest muscle growth, or back muscle growth. The scale can measure strength of different parts of the body.

Weight loss verification system 100 may also include a lock feature that locks a video once it has been submitted. A locked video is secured such that it cannot thereafter be altered or deleted. An indication that a submitted video is locked may appear to users. The user that uploaded the video may be able to "unlock" the video to edit or delete the video, allowing for a new weigh-in video to be submitted. Videos can also be pre-verified. For example, a user's weigh-in may be monitored by a healthcare professional or a representative of the weight loss contest operator to ensure the proper procedure is followed. Monitored weigh-ins can also be scheduled for random or specified times. Once submitted, pre-verified weigh-ins may include a badge or other indication that the weigh-in has been pre-verified. This ensures to users that both their own submissions and submissions by other users cannot be tampered with or altered in any way. The uploading of videos and accessing of uploaded videos may be tracked by the user's IP Address, Internet Service Provider, and log-in. A user can generate a unique password from their account to allow third parties to view submissions.

Particular weigh-ins throughout the weight loss contest may be more important than others and have special procedures. For example, the first and last weigh-ins submitted by a user, which are used to determine the total amount of weight lost during the contest, may be more important than weigh-ins submitted in the middle of the contest. Thus, a user may be required to have the first and last weigh-ins pre-verified or otherwise performed under some sort of supervision or special procedure. Further, weight lost contests having a prize over a certain dollar amount may require special procedures for weigh-ins or may require a doctor to conduct a physical for each user.

According to some aspects of the present disclosure, a scale of the present disclosure can include an input device (e.g., a keypad, a touch screen, etc.) permitting a user of the scale to type in or otherwise enter a unique weigh-in authentication code received by the user during an initial sign up and/or received by the user each time the user conducts a verified weigh in sequence. For example, the user can receive the code via text message, email, popup alert, phone call, by logging into the user's account, via the weigh in application on the user's mobile electronic device, etc. or any combination thereof. Alternatively or additionally, the unique weigh-in authentication code can be entered by the user into an application executing on the user's mobile electronic device and/or via a web portal (e.g., accessed via the user's mobile electronic device, tablet, desktop computer, etc.). In some implementations, the user enters the code to permit the verified weigh-in to occur (e.g., to permit the scale to determine the user's weight, to permit the camera to record video of the user conducting the verified weigh in, etc., or a combination thereof). The input device (e.g., keypad, touch screen etc.) can be on the front, back, and/or sides of the scale housing.

According to some such implementations, the scale does not include such a keypad type input device. Rather, the code can be input into via scale and/or received by the scale by simply pressing the scale (e.g., with the user's foot/toe/hand/finger) corresponding to numbers (e.g., three taps registers the number 3) and/or a code (e.g., Morse code where, for example, two short taps followed by a long tap is the code) or other pattern representing/corresponding to the unique weigh-in authentication code.

According to some implementations, a scale of the present disclosure includes a beacon that transmits a unique scale identifier that identifies the scale. When a user creates a profile/account, the user can pair their account to their scale and its unique scale identifier (e.g., via a learning process) such that the scale is associated with the user's mobile electronic device (e.g., cell phone) and/or account. The association of the unique scale identifier/scale can occur during the first verified weigh-in and/or the initial account setup for the user.

In some implementations, a beacon of a scale transmits a wireless signal that is associated with a unique scale identifier. Mobile electronic devices in the surrounding area receive the wireless beacon signal and in some instances transmit a responsive message to the scale identifying the mobile electronic device, the user of the mobile electronic device, and/or the account associated with the user. As such, the scale is able to track the identify of mobile electronic devices/users in the surrounding area of the scale.

In some implementations, because the scale is tied to the account/phone of a specific user, when a user conducts a verified weigh-in, the application software can check to ensure the scale being used is the one associated with the user's account/mobile electronic device and if not, an electronic flag will be included in the data file sent to the server during verification. The flag can cause the data file to be highlighted as one that should be reviewed by the server for further authentication and/or by other participants in a weight loss competition with the user having the flagged data file. That is, in some implementations, a user is only permitted to use a scale previously associated with the user's account to aid in the verification process of the weigh ins.

According to some implementations, in a public location, such as, for example, a mall, a store, a school, a place of work, a gym, etc., or a combination thereof, a multitude of scales (or just one scale per location) according to the present disclosure, each having its own beacon, are included in a weigh in station. The weigh in station further includes one or more display devices (e.g., one for each scale, one for each location, etc.). According to some such implementations, when a user goes to weigh-in using one of the scales, the beacon of the scale is received by the mobile electronic device of the user (associated with an account) and uploaded (e.g., via the software application executing on the mobile electronic device of the user) to the server (which is coupled to the scales of the weigh in station). As such, the server is able to identify the users of the weigh in station and associate the user with the scale located at the weigh in station. Further the server is able to cause information be displayed on one or more of the display devices of the weigh in station, such as, for example, weigh in information, personal information, account information, contest standings, etc., or any combination thereof.

According to some aspects, a unique identifier of a mobile electronic device (e.g., MAC address, EIN, etc.) associated with a user or participant of a weight loss competition is associated with an account of the user for use in verifying and/or increasing the reliability of determined data (e.g., weight data) used in one or more weight loss contests. That is, in some implementations, the data file generated includes the unique identifier of the mobile electronic device that was user to generate the data file. During the verification process (e.g., implemented by the server), the unique identifier of the mobile electronic device is compared with the user's account, which includes the unique identifier of the mobile electronic device entered during the initial sign up process, to confirm a match. If the two unique identifiers do not match the data file is flagged and further verification is required.

According to some implementations, one or more scales of the present disclosure include a beacon built therein that is in communication with a server. The beacon permits the server to receive information identifying mobile electronic devices and/or users with an account that enter within a range of the beacon and/or the scale. That is, the scale and/or server is able to detect mobile devices with a range of the beacon and/or a scale and take one or more actions based on that detection. For example, the scale and/or server can cause a push notification to be sent to the mobile electronic device with a message to conduct a verified weigh in.

According to some implementations, a scale includes a beacon that broadcasts out a unique identifier and a mobile electronic device associated with a user account receives the unique identifier, which causes the mobile electronic device to push data (e.g., a location associated with the mobile electronic device, a location associated with the scale, a time, an identifier associated with the mobile electronic device, an identifier associated with the scale, etc., or any combination thereof) to a server.

According to some implementations, a scale is connected to the internet (e.g., via a wireless and/or wired connection) such that the scale is configured to transmit data (e.g., a location associated with the mobile electronic device, a location associated with the scale, a time, an identifier associated with the mobile electronic device, an identifier associated with the scale, etc., or any combination thereof) to a server over the internet.

According to some implementations, a user or participant in a weight loss competition needs to conduct a verified weigh in. The participant initially creates a profile/account that includes one or more face/body image(s) and/or videos of the participant (e.g., wearing a specified set of clothes). After creating the account, the participant conducts a verified weigh in according to aspects of the present disclosure. In some implementations, during every weigh-in of the participant, a comparison of newly generated/received weigh in video/image(s) is made with the profile image(s) and/or video originally stored when the account was created to authenticate the person in the images/video that is weighing in. In some implementations, machine learning is used to predict, based at least in part on the amount of weight recorded during a weigh in, what the participant's face/body should look like. Further, adjustments to the original profile images/video can be automatically made over time based on artificial intelligence that learns the person's face/body with each subsequent weigh in to make more reliable authentications of the participant.

According to some implementations of the present disclosure, a scale includes a camera (e.g., integrated therein or separate and distinct therefrom) positioned to capture images/video in front of, behind, to the side of, the scale (e.g., an area adjacent to one or more edges of the scale but not including an area directly above the scale such as a person standing on the scale to weigh themselves). In some such implementations, the camera is referred to as a front-facing camera that is used to capture, for example, a participant in a weight loss competition about to conduct a weigh-in that stands in front of the scale. The participant may be directed to and/or required to make a set of movements or gestures within a field of view of the front-facing camera prior to stepping on to the scale. In some such implementations, the scale causes audible instructions (e.g., "turn around 360 degrees," "jump up three times," do two jumping jacks, "touch your ties," etc. or any combination thereof) to be played via a speaker of the scale. In some such implementations, the audible instructions are played via a speaker of an electronic device, such as, for example, a mobile phone connected to the scale. After the participant is within the field of view of the front-facing camera, the participant then walks towards scale and steps onto the scale for the weight to be recorded/determined. As such, the camera is able to capture the participate prior to the weight being determined and also capture the participant engaging the scale immediately prior to (e.g., within four second, or within three seconds, or within two seconds, or within one second, within half of a second, or within a quarter of a second, etc.) the participant's weighed being determined. In some implementations, responsive to a weight of the participant being recorded by the scale within a set amount of time (e.g., less than five seconds) from when the user stepped over the camera and onto the scale, the weight is verified as being associated with the person captured in the images/video. As discussed above, the camera can be attached to a back end of the scale such that the person just walks straight and steps onto the scale without having to turn 180 degrees to have the display of the scale be readable (e.g., not upside down).

According to some implementations, methods of conducting verified weigh in sessions of a participant of a weight loss competition leverage the use of two clocks. For example, a first internal clock of mobile electronic device (e.g., cellphone) is used to time when a video of the participant conducting a weigh in session was created (e.g., the time form when a participant steps onto a scale to the time when the weight of the user is determined by the scale (or a short while thereafter, such as, for example, one second, two seconds, etc.) and a second internal clock of a scale is used to obtain a time when the weight of participant was determined by the scale. The two times or ranges of time can be compared to ensure that the time the scale determined the weight corresponds with (e.g., is within) the range of time that the video was generated. By confirming the correspondence of the two times, the accuracy and/or veracity of the determined data (e.g., weight data) is improved.

According to some implementations, during, for example, a first verified weigh in session of a participant and/or during an initial account creation for the participant, a first internal clock of a mobile electronic device (e.g., cellphone) is synced with a second internal clock of a scale. In some such implementations, even if the times are off (e.g., do not correspond with one another, or differ by one second, or differ by one minute, or differ by an hour, etc.) the difference between the first and second internal clocks is recorded and used in future sessions to aid in ensuring reliability of the session and the data acquired during the session. For example, if the first internal clock of the mobile electronic device registers or sends a time of 12:01:05 pm and the second internal clock of the scale registers or sends a time of 12:02:15 pm, the one minute and ten second difference is recorded and used during subsequent sessions to ensure that the weight determined by the scale corresponds with the time that the visual video clip is created on the mobile electronic device. That is, the system knows that during subsequent sessions, at no time should there be a time difference between the scale and mobile electronic device that varies (e.g., more than a predetermined acceptable amount, such as, for example, 0.01 seconds, or 0.1 seconds, or 1 second, or two seconds, etc.) from one minute and ten seconds from the time of each weigh in. In some such implementations, a variance of the clocks that is greater than the acceptable variance will cause an alert or alarm to be trigger, which may cause additional verification steps to be required for the session/weigh in.

According to some implementations, during an initial account setup and/or scale setup (e.g., when pairing a scale to the user's mobile electronic device), the internal scale clock is synced (e.g., made to match) with the internal mobile electronic device clock. That is, after the scale is paired with a mobile electronic device, the internal clock of the scale should match the internal clock of the mobile electronic device when comparing time stamps of the two in the data file.

According to some implementations, a scale of the present disclosure includes a display device that displays a video that mirrors the display or at least a portion of the display of a mobile electronic device recording a video of the participant conducting a verified weigh in session. As such, the participant can view the video of the weigh in session by looking down toward her toes instead of trying to see the display of the mobile electronic device.

While the present disclosure discusses scales and verified weigh in sessions, the present disclosure can be applied to verifying any measurement of a person. For example, the aspects of the present disclosure can be applied to conduct a verified biomeasurement of a user where one or more biomeasurments and/or health data and/or health related data is obtained that is associated with the user and/or indicative of one or more biomeasurements of the user. In some such implementations, the scale of the present disclosure can be substituted for a biomeasurement device, such as, for example, a scale, a Body Mass Index (BMI) sensor device, a bio impedance sensor device, a blood glucose meter device, a blood A1C meter device, a blood cholesterol meter device, a heart rate monitor device (e.g., for measuring rest heart rates, peak heart rates, heart rates during various levels of activity, etc.), a blood pressure monitor device, a digital caliper device (e.g., for measuring portions of arms, legs, stomachs, etc.), a respiration monitor device (e.g., for measuring breathing via a thermal sensor and/or via a displacement sensor), a finger print scanner, a toe print scanner, a step monitor/sensor, an activity monitor/sensor, a perspiration and/or hydration sensor device (e.g., for measuring sweat, etc.), an EKG sensor(s) device, or any combination thereof. Such biomeasurement devices can be used to obtain a variety of biomeasurements and/or health data, such as, for example, one or more weights/mass, one or more Body Mass Indexes (BMI), one or more bio impedance measurements, one or more blood glucose measurements, one or more A1C measurements, one or more cholesterol measurements, one or more heart rates, one or more blood pressures, one or more digital caliper measurements, one or more respiration rates, one or more fingerprints, one or more toe prints, one or more step counts, one or more activity levels, one or more perspiration and/or hydration level measurements, one or more EKG readings, or any combination thereof.

According to some implementations, use of the present disclosure to conduct verified biomeasurements can be used in telemedicine practices such that doctors and/or providers can be assured that the data received is/was verified/confirmed as belonging to the patient assumed to have sent the data. In some instances, when a parent communicates with a child's doctor or a spouse's doctor, mix-ups that might have otherwise occurred by associating the data with the sender as opposed to the individual associated with the health data can be reduced and or prevented by verifying the health data/biomeasurments using the methods of the present disclosure. Further, insurance companies can leverage the benefits of verified biomeasurements to ensure that the insured individual is the individual that is providing the health data. As such, insurance companies can offer more customized plans based on periodic verified health data packets (e.g., data files) including one or more biomeasurements associated with the insured individual.

The present disclosure includes description of many scales and biomeasurement devices and many features of the same. Any combination of the features of one implementation can be used with any combination of features of other implementation described herein.

While the present disclosure has been described with reference to one or more particular embodiments and implementations, those skilled in the art will recognize that many changes may be made thereto without departing from the spirit and scope of the present disclosure. Each of these embodiments and implementations and obvious variations thereof is contemplated as falling within the spirit and scope of the present disclosure, which is set forth in the claims that follow.

What is claimed is:

1. A method of conducting a verified weigh-in, the method comprising:
   receiving at a first time, via an electronic scale supporting a user thereon, a first indication to begin a first verified weight sequence;
   responsive to the first indication to begin the first verified weight sequence:
      determining a first body weight of the user supported by the electronic scale device;
      receiving, via an electronic device, first image data that is reproducible as a first visual image of at least a portion of the user supported on the housing of the scale; and
      analyzing the first image data using recognition software to produce a first user appearance profile;
   producing an expected user appearance profile based on at least the first user appearance profile, wherein the expected user appearance profile is based on the first user appearance profile, the determined first body weight of the user, and a time difference between the first time and a second time;
   receiving at the second time, via the electronic scale supporting the user thereon, a second indication to begin a second verified weight sequence; and
   responsive to the second indication to begin the second verified weight sequence;
      determining a second body weight of the user supported by the electronic scale device;
      receiving, via the electronic device, second image data that is reproducible as a second visual image of at least a portion of the user supported on the housing of the scale;
      analyzing the second image data using recognition software to produce a second user appearance profile; and
      comparing the second user appearance profile to the expected user appearance profile.

2. The method of claim 1, wherein the recognition software includes facial recognition software, body recognition software, or both facial recognition software and body recognition software.

3. The method of claim 1, wherein the comparison between the second user appearance profile and the expected user appearance profile is used to verify the second verified weight sequence.

4. The method of claim 1, wherein the receiving the first image data occurs at about the same time as the first time and wherein the receiving the second image data occurs at about the same time as the second time.

\* \* \* \* \*